(12) United States Patent
Hoshino

(10) Patent No.: US 10,502,671 B2  
(45) Date of Patent: Dec. 10, 2019

(54) VISCOSITY MEASURING METHOD AND VISCOSITY MEASURING APPARATUS

(71) Applicant: AOHATA CORPORATION, Takehara-Shi (JP)

(72) Inventor: Takayoshi Hoshino, Takehara (JP)

(73) Assignee: Aohata Corporation, Takehara-Shi (JP)

( * ) Notice: Subject to any disclaimer, the term of this patent is extended or adjusted under 35 U.S.C. 154(b) by 74 days.

(21) Appl. No.: 15/567,439

(22) PCT Filed: Apr. 28, 2016

(86) PCT No.: PCT/JP2016/063318  
§ 371 (c)(1),  
(2) Date: Oct. 18, 2017

(87) PCT Pub. No.: WO2016/178407  
PCT Pub. Date: Nov. 10, 2016

(65) Prior Publication Data  
US 2018/0106711 A1 Apr. 19, 2018

(30) Foreign Application Priority Data  
May 7, 2015 (JP) ................................ 2015-095077

(51) Int. Cl.  
*G01N 11/10* (2006.01)  
*G01N 11/00* (2006.01)

(52) U.S. Cl.  
CPC ...... *G01N 11/10* (2013.01); *G01N 2011/0006* (2013.01); *G01N 2011/0026* (2013.01)

(58) Field of Classification Search  
CPC ......... G01N 11/10; G01N 11/12; G01N 3/303  
See application file for complete search history.

(56) References Cited

U.S. PATENT DOCUMENTS 1,651,596 A * 12/1927 Hall ..................... G01N 11/10  
                                                                      73/150 R  
4,011,901 A * 3/1977 Flemings ................ B22D 2/00  
                                                                   164/457

(Continued)

FOREIGN PATENT DOCUMENTS

| JP | 03140839 A | * | 6/1991 |
| JP | 3446117 B2 | | 9/2003 |
| JP | 2014-055928 A1 | | 3/2014 |
| JP | 5596244 B1 | | 9/2014 |

OTHER PUBLICATIONS

International Search Report and Written Opinion (Application No. PCT/JP2016/063318) dated Jul. 26, 2016.

(Continued)

*Primary Examiner* — David A Rogers  
(74) *Attorney, Agent, or Firm* — Burr & Brown, PLLC

(57) ABSTRACT

A viscosity measuring method includes: immersing a plunger into a sample contained in a cylindrical container by an initial depth $L_0$; further immersing the plunger at a velocity $v_{p1}$ by a distance $\Delta L_1$, and measuring a force applied to the plunger; obtaining first peak value $F_{T1}$ and a first convergent value $F_{Te1}$ of the force; returning the plunger to the initial depth $L_0$; further immersing the plunger at a velocity $v_{p2}$ by a distance $\Delta L_2$, and measuring a force applied to the plunger; obtaining a second peak value $F_{T2}$ and a second convergent value $F_{Te2}$ of the force; obtaining a flow behavior index n; and calculating an apparent viscosity $\mu_a$ of the sample based on Expression (1).

21 Claims, 9 Drawing Sheets

(56) References Cited

U.S. PATENT DOCUMENTS

| | | | | |
|---|---|---|---|---|
| 4,484,468 | A * | 11/1984 | Gau | G01N 11/14 |
| | | | | 702/50 |
| 4,596,137 | A * | 6/1986 | Fisher | G01N 13/00 |
| | | | | 73/54.36 |
| 6,145,373 | A * | 11/2000 | Tymchuck | G01N 11/14 |
| | | | | 73/54.28 |
| 7,614,285 | B2 * | 11/2009 | Airey | G01N 11/10 |
| | | | | 73/54.23 |
| 7,681,437 | B2 * | 3/2010 | Brinz | G01N 11/04 |
| | | | | 73/54.14 |
| 8,573,029 | B2 * | 11/2013 | Kawamura | G01N 11/12 |
| | | | | 73/12.06 |
| 2001/0037673 | A1 * | 11/2001 | Jackson | G01N 11/10 |
| | | | | 73/54.23 |
| 2008/0236254 | A1 * | 10/2008 | Airey | G01N 11/10 |
| | | | | 73/54.23 |
| 2011/0226046 | A1 * | 9/2011 | Giardino | G01N 3/303 |
| | | | | 73/82 |
| 2012/0186326 | A1 * | 7/2012 | Kawamura | G01N 11/12 |
| | | | | 73/12.01 |
| 2014/0190242 | A1 * | 7/2014 | Giardino | G01N 3/303 |
| | | | | 73/54.36 |
| 2015/0338332 | A1 | 11/2015 | Hoshino | |

OTHER PUBLICATIONS

Morgan, R.G., et al., "Mathematical Analysis of a Simple Back-Extrusion Rheometer," *American Society of Agricultural Engineers*, Paper No. 79-6001 (1979).

Osorio, F.A., et al., "Back Extrusion of Power Law Fluids," *Journal of Texture Studies*, 18 (1987), pp. 43-63.

Osorio, F.A., et al., "Evaluating Herschel-Bulkley Fluids with the Back Extrusion (Annular Pumping) Technique," *Rheologica Acta*, vol. 30, No. 6 (1991), pp. 549-558.

Fredrickson, A., et al., "Non-Newtonian Flow in Annuli," *Industrial & Engineering Chemistry*, vol. 50, No. 3 (Mar. 1958), pp. 347-352.

Hanks, Richard W., "The Axial Laminar Flow of Yield-Pseudoplastic Fluids in a Concentric Annulus," *Ind. Eng. Chem. Process Des. Dev.*, vol. 18, No. 3 (1979), pp. 488-493.

Hoshino, Takayoshi, et al., "Proposal of Short Back Extrusion Method for Enabling Consecutive Viscosity Measurements of High-Viscosity Newtonian Fluid," *Journal of the Japanese Society for Food Science and Technology*, vol. 60, No. 2 (Feb. 15, 2013), pp. 100-109.

English translation of International Preliminary Report on Patentability (Chapter I) (Application No. PCT/JP2016/063318) dated Nov. 16, 2017, 6 pgs.

* cited by examiner

VISCOSITY MEASURING METHOD AND VISCOSITY MEASURING APPARATUS

TECHNICAL FIELD

The present invention relates to a viscosity measuring method and a viscosity measuring apparatus.

BACKGROUND ART

Physical properties of food are characteristic values important to controlling food qualities in processing, distribution and consumption. In particular if a viscosity can be easily measured, it is possible to know not only processing aptitudes for cooking, filling and so on but also textures and easiness in handling, as well as comparison with another food can be facilitated.

There are various types of viscosity measuring apparatuses, and the types are roughly classified into a rotation type and a translation type.

The rotation type viscosity measuring apparatus is advantageous in providing a simple measurement at low cost, and is suited for measuring a uniform sample having a low viscosity. However, when a sample having a high viscosity such as a gel is measured by the rotation-type viscosity measuring apparatus, an internal structure of the sample varies because of a "shear deformation" or vibrations give thereto until a measurement value becomes stable. Thus, there is a problem in that a viscosity of the sample is measured to be lower than an actual viscosity.

On the other hand, the translation-type viscosity measuring apparatus is advantageous in having a simple apparatus structure, without any rotating and driving unit. There are a translation-type viscosity measuring apparatus of a parallel plate type and a translation type viscosity measuring apparatus of a concentric cylinder type. Non-Patent Documents 1 to 4 disclose a viscosity measuring method using a viscosity measuring apparatus of a concentric cylinder type.

The method (referred to also as back extrusion (BE) method) disclosed in the Non-Patent Documents 1 to 3 is a typical translation type viscosity measuring method. In this viscosity measuring method, a cylindrical plunger is pushed into a sample contained in a cylindrical container from outside the sample, the sample is made to flow upward in an annular gap part between the container and the plunger, and a viscosity is calculated from a stress-time curve applied to the plunger. Although this method can analyze from a Newtonian fluid up to a Herschel-Bulkley fluid, it is necessary to increase a deformation degree applied to the sample in order to obtain a steady flow in the annular part, which deformation for measurement destroys the structure of the sample. Thus, this method cannot measure the same sample consecutively. In addition, when a sample has a high viscosity, it is necessary to carefully remove the sample adhering to the container and the plunger after measurement. Thus, the operation is complicated and a longer time is needed. Moreover, since the method is somewhat inferior in measurement precision, the method is not so generally prevalent.

On the other hand, the method (referred to also as short back extrusion (SBE) method) disclosed in the Non-Patent Document 4 by the present inventors is a method wherein a cylindrical plunger is previously immersed by a predetermined depth into a sample contained in a cylindrical container, the plunger is further pushed thereinto from the original position by a slight distance to generate a steady flow in an annular part, and a viscosity is measured from a stress-time curve applied to the plunger. In this method, the annular part between the plunger and the container has been already filled with the sample before the plunger is pushed thereinto, which is different from the BE method. Thus, even if a movement distance of the plunger is short, a steady flow can be generated. Thus, since an amount of the sample adhering to the plunger and the container is small, consecutive measurement is enabled.

The present inventors have already proposed a method of analyzing a Newtonian fluid and a power-law fluid (see Patent Documents 1 and 2). This method can perform viscosity measurement that is more precise than the BE method. However, a method of analyzing Herschel-Bulkley fluid by the SBE method is not known.

By the way, a non-Newtonian fluid is a fluid whose viscosity is dependent on a "shear rate". A viscosity of the non-Newtonian fluid is represented as an apparent viscosity obtained by dividing a "sheer stress" by a "shear rate". In addition, the power-law fluid is a non-Newtonian fluid whose minimum value of the shear stress (referred to as yield stress), which is necessary to start flow, is zero. The Herschel Bulkley fluid is a non-Newtonian fluid whose yield stress is larger than zero.

PATENT DOCUMENTS

Patent Document 1: JP2014-055928A
Patent Document 2: JP5596244B

NOT-PATENT DOCUMENTS

Non-Patent Document 1: Morgan, R. G., Suter, D. A., Sweat, V. E., Mathematical analysis of a simple back-extrusion rheometer. American society of agricultural engineers, 79, 6001, (1979)

Non-Patent Document 2: Osorio, F. A., Steffe, J. F., Back extrusion of power law fluids. J. Texture Stud., 18, 43-63 (1987)

Non-Patent Document 3: Osorio, F. A., Steffe, J. F., Evaluating Herschel-Bulkley fluids with the back extrusion (annular pumping) technique. Rheologica Acta, 30, 549-558 (1991)

DISCLOSURE OF THE INVENTION

Problem to be Solved by the Invention

The object of the present invention is to provide a viscosity measuring method and a viscosity measuring apparatus capable of precisely measuring an apparent viscosity of a sample of a non-Newtonian fluid.

Means for Solving the Problem

A viscosity measuring method according to the present invention is a method of measuring an apparent viscosity of a sample of non-Newtonian fluid comprising:

(A) a step in which a plunger having an outer radius $R_i$ is immersed into a sample contained in a cylindrical container having an inner radius $R_O$, coaxially with the cylindrical container by an initial depth $L_0$ and stopped thereat, the outer radius $R_i$ of the plunger being smaller than the inner radius $R_O$ of the cylindrical container;

(B) a step in which the plunger is further immersed into the sample coaxially with the cylindrical container at a first relative movement velocity $v_{p1}$ by a first relative movement distance $\Delta L_1$, and during the further immersing operation and after the further immersing operation, a force applied to the plunger from the sample is measured with a passage of time;

(C) a step in which a first peak value $F_{T1}$ and a first convergent value $F_{Te1}$ of the force applied to the plunger from the sample are obtained, based on measured values of the force caused by the relative movement of the plunger at the first relative movement velocity $v_{p1}$;

(D) a step in which the plunger is returned coaxially with the cylindrical container to the initial depth $L_0$ and stopped thereat;

(E) a step in which the plunger is further immersed into the sample coaxially with the cylindrical container at a second relative movement velocity $v_{p2}$ by a second relative movement distance $\Delta L_2$, and during the further immersing operation and after the further immersing operation, a force applied to the plunger from the sample is measured with a passage of time;

(F) a step in which a second peak value $F_{T2}$ and a second convergent value $F_{Te2}$ of the force applied to the plunger from the sample are obtained, based on measured values of the force caused by the relative movement of the plunger at the second relative movement velocity $v_{p2}$;

(G) a step in which, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n is obtained; and (H) a step in which, when the first relative movement velocity $v_{p1}$ is represented as $v_p$, the first relative movement distance $\Delta L_1$ is represented as $\Delta L$, the first peak value $F_{T1}$ is represented as $F_T$, and the first convergent value $F_{Te1}$ is represented as $F_{Te}$ or when the second relative movement velocity $v_{p2}$ is represented as $v_p$, the second relative movement distance $\Delta L_2$ is represented as $\Delta L$, the second peak value $F_{T2}$ is represented as $F_T$, and the second convergent value $F_{Te2}$ is represented as $F_{Te}$, an apparent viscosity $\mu_a$ of the sample is calculated based on the $v_p$, the $\Delta L$, the $F_T$, the $F_{Te}$, the plunger ratio $\kappa$, the flow behavior index n, a density $\rho$ of the sample, a gravitational acceleration g, and the following Expression (1):

[NO 1]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w P R_0}{2}, \frac{d\gamma}{dt} = \left(\frac{\lambda^2}{\kappa} - \kappa - T_0\right)^s \left(\frac{PR_0}{2K}\right)^s, \quad (2)$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx\right\}\kappa^2 -$$

$$\int_\kappa^{\lambda_-}(\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx, \quad (3)$$

-continued $$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

In the viscosity measuring method according to the present invention, the first relative movement distance $\Delta L_1$ and the second relative movement distance $\Delta L_2$ may be smaller than the initial depth $L_0$.

In the viscosity measuring method according to the present invention, in the step of obtaining the flow behavior index n, before obtaining the flow behavior index n, it may be judged whether the convergent value $F_{Te}$ of the force applied to the plunger from the sample at the first relative movement velocity $v_{p1}$ or the second relative movement velocity $v_{p2}$ is larger or not than a buoyancy force $F_b$ applied to the plunger from the sample, and when the convergent value $F_{Te}$ is judged to be larger than the buoyancy force $F_b$, the process for obtaining the flow behavior index n is performed.

In the viscosity measuring method according to the present invention, the relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; the plunger ratio $\kappa$; and the flow behavior index n of the sample may include the above Expressions (2) to (5) and the following Expression (6):

[NO 2]

$$s = \frac{1}{n} = \frac{\ln\left(\frac{v_{p2}/\Phi_2}{v_{p1}/\Phi_1}\right)}{\ln\left(\frac{F_{cb2}/(L_0 + L_{2\_2})\lambda_2^2}{F_{cb1}/(L_0 + L_{2\_1})\lambda_1^2}\right)}. \quad (6)$$

In the viscosity measuring method according to the present invention, the step of obtaining the flow behavior index n may include:

a step in which a provisional flow behavior index $n_a$ is determined;

a step in which, based on the above Expressions (3) to (5) established among: the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio $\kappa$; and a first dimensionless coordinate $\lambda_1$; or based on a graph or a table created based on the above Expressions (3) to (5), the first dimensionless coordinate $\lambda_1$ is obtained;

a step in which, based on the above Expression (2) established among the provisional flow behavior index $n_a$, the first dimensionless coordinate $\lambda_1$ and a first dimensionless flow velocity $\Phi_1$, or based on a graph or a table created based on the above Expression (2), the first dimensionless flow velocity $\Phi_1$ is obtained;

a step in which, based on the above Expressions (3) to (5) established among: the provisional flow behavior index $n_a$;

the second relative movement distance $\Delta L_2$, the second peak value $F_{T2}$ and the second convergent value $F_{Te2}$, at the second relative movement velocity $v_{p2}$; the plunger ratio $\kappa$; and a second dimensionless coordinate $\lambda_2$; or based on a graph or a table created based on the above Expressions (3) to (5), the second dimensionless coordinate $\lambda_2$ is obtained;

a step in which, based on the above Expression (2) established among the provisional flow behavior index $n_a$, the second dimensionless coordinate $\lambda_2$ and a second dimensionless flow velocity $\Phi_2$, or based on a graph or a table created based on the above Expression (2), the second dimensionless flow velocity $\Phi_2$ is obtained;

a step in which a flow behavior index n is obtained based on: the first dimensionless coordinate $\lambda_1$ and the first dimensionless flow velocity $\Phi_1$ at the first relative movement velocity $v_{p1}$; the second dimensionless coordinate $\lambda_2$ and the second dimensionless flow velocity $\Phi_2$ at the second relative movement velocity $v_{p2}$; and the above Expression (6); and a step in which the method returns to the step of determining a provisional flow behavior index $n_a$, when the obtained flow behavior index n is compared to the provisional flow behavior index $n_a$ to find out that the obtained flow behavior index n is different from the provisional flow behavior index $n_a$.

A viscosity measuring method according to the present invention is a method of measuring an apparent viscosity of a sample of non-Newtonian fluid comprising:

(A) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;

(B) a step in which the plunger is further immersed into the sample coaxially with the cylindrical container at a first relative movement velocity $v_{p1}$ by a relative movement distance $\Delta L$, and during the further immersing operation and after the further immersing operation, a force applied to the plunger from the sample is measured with a passage of time;

(C) a step in which a first peak value $F_{T1}$ and a first convergent value $F_{Te1}$ of the force applied to the plunger from the sample are obtained, based on measured values of the force caused by the relative movement of the plunger at the first relative movement velocity $v_{p1}$;

(D) a step in which the plunger is returned coaxially with the cylindrical container to the initial depth $L_0$ and stopped thereat;

(E) a step in which the plunger is further immersed into the sample coaxially with the cylindrical container at a second relative movement velocity $v_{p2}$ by the relative movement distance $\Delta L$, and during the further immersing operation and after the further immersing operation, a force applied to the plunger from the sample is measured with a passage of time;

(F) a step in which a second peak value $F_{T2}$ and a second convergent value $F_{Te2}$ of the force applied to the plunger from the sample are obtained, based on measured values of the force caused by the relative movement of the plunger at the second relative movement velocity $v_{p2}$;

(G) a step in which, based on a predetermined relationship established among: the first peak value $F_{T1}$ and the first convergent value $F_{Te1}$ at the first relative movement velocity $v_{p1}$; the second peak value $F_{T2}$ and the second convergent value $F_{Te2}$ at the second relative movement velocity $v_{p2}$; the relative movement distance $\Delta L$; a plunger ratio $\kappa = R_i/R_0$; and a flow behavior index n of the sample; the flow behavior index n is obtained;

(H) a step in which, when the first relative movement velocity $v_{p1}$ is represented as $v_p$, the first peak value $F_{T1}$ is represented as $F_T$, and the first convergent value $F_{Te1}$ is represented as $F_{Te}$, or when the second relative movement velocity $v_{p2}$ is represented as $v_p$, the second peak value $F_{T2}$ is represented as $F_T$, and the second convergent value $F_{Te2}$ is represented as $F_{Te}$, an apparent viscosity $\mu_a$ of the sample is calculated based on the $v_p$, the $F_T$, the $F_{Te}$, the relative movement distance $\Delta L$, the plunger ratio $\kappa$, the flow behavior index n, a density $\rho$ of the sample, a gravitational acceleration g, and the following Expression (1):

[NO 3]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w P R_0}{2}, \frac{d\gamma}{dt} = \left(\frac{\lambda^2}{\kappa} - \kappa - T_0\right)^s \left(\frac{P R_0}{2}\right)^s, \quad (2)$$

$$K = \frac{P R_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx\right\}\kappa^2 -$$

$$\int_\kappa^{\lambda_-}(\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx, \quad (3)$$

$$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i (L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

In addition, a viscosity measuring method according to the present invention is a method of measuring an apparent viscosity of a sample of non-Newtonian fluid comprising:

(A) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;

(B) a step in which the plunger is further immersed into the sample coaxially with the cylindrical container at a first relative movement velocity $v_{p1}$ by a first relative movement distance $\Delta L_1$, and during the further immersing operation and after the further immersing operation, a force applied to the plunger from the sample is measured with a passage of time;

(C) a step in which a first peak value $F_{T1}$ and a first convergent value $F_{Te1}$ of the force applied to the plunger from the sample are obtained, based on measured values of the force caused by the relative movement of the plunger at the first relative movement velocity $v_{p1}$;

(D) a step in which the plunger is returned coaxially with the cylindrical container to the initial depth $L_0$ and stopped thereat;

(E) a step in which the plunger is further immersed into the sample coaxially with the cylindrical container at a second relative movement velocity $v_{p2}$ by a second relative movement distance $\Delta L_2$, and during the further immersing operation and after the further immersing operation, a force applied to the plunger from the sample is measured with a passage of time;

(F) a step in which a second peak value $F_{T2}$ and a second convergent value $F_{Te2}$ of the force applied to the plunger from the sample are obtained, based on measured values of the force caused by the relative movement of the plunger at the second relative movement velocity $v_{p2}$;

(G) a step in which, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n is obtained;

(H) a step in which the plunger is returned coaxially with the cylindrical container to the initial depth $L_0$ and stopped thereat;

(I) a step in which the plunger is further immersed into the sample coaxially with the cylindrical container at a third relative movement velocity $v_{p3}$ by a third relative movement distance $\Delta L_3$, and during the further immersing operation and after the further immersing operation, a force applied to the plunger from the sample is measured with a passage of time;

(J) a step in which a third peak value $F_{T3}$ and a third convergent value $F_{Te3}$ of the force applied to the plunger from the sample are obtained, based on measured values of the force caused by the relative movement of the plunger at the third relative movement velocity $v_{p3}$;

(K) a step in which, when the third relative movement velocity $v_{p3}$ is represented as $v_p$, the third relative movement distance $\Delta L_3$ is represented as $\Delta L$, the third peak value $F_{T3}$ is represented as $F_T$ and the third convergent value $F_{Te3}$ is represented as $F_{Te}$, an apparent viscosity $\mu_a$ of the sample is calculated based on the $v_p$, the $\Delta L$, the $F_T$ and the $F_{Te}$, the plunger ratio $\kappa$, the flow behavior index n, a density $\rho$ of the sample, a gravitational acceleration g, and the following Expression (1):

[NO 4]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w P R_0}{2}, \frac{d\gamma}{dt} = \left(\frac{\lambda^2}{\kappa} - \kappa - T_0\right)^s \left(\frac{PR_0}{2K}\right)^s, \quad (2)$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx\right\}\kappa^2 -$$

$$\int_\kappa^{\lambda_-}(\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx, \quad (3)$$

$$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1-\kappa^2}.$$

A viscosity measuring apparatus according to the present invention is a viscosity measuring apparatus comprising:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container;

a measuring unit disposed on the plunger and configured to measure a force applied to the plunger from the sample; and a control unit configured to control the driving unit;

wherein:

the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control unit is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control unit is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control unit is further configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa=R_i/R_0$; and a flow behavior index n of the sample; the flow behavior index n; and the control unit is further configured to calculate, when the first relative movement velocity $v_{p1}$ is represented as $v_p$, the first relative movement distance $\Delta L_1$ is represented as $\Delta L$, the first peak value $F_{T1}$ is represented as $F_T$, and the first convergent value $F_{Te1}$ is represented as $F_{Te}$, or when the second relative movement velocity $v_{p2}$ is represented as $v_p$, the second relative movement distance $\Delta L_2$ is represented as $\Delta L$, the second peak value $F_{T2}$ is represented as $F_T$, and the second convergent value $F_{Te2}$ is represented as $F_{Te}$, an apparent viscosity $\mu_a$ of the sample based on the $v_p$, the $\Delta L$, the $F_T$, the $F_{Te}$, the plunger ratio $\kappa$, the flow behavior index n, a density $\rho$ of the sample, a gravitational acceleration g, and the following Expression (1):

[NO 5]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w P R_0}{2}, \frac{d\gamma}{dt} = \left(\frac{\lambda^2}{\kappa} - \kappa - T_0\right)^s \left(\frac{PR_0}{2K}\right)^s, \quad (2)$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_\kappa^{\lambda_-}(\lambda^2 - x^2 - T_0 x)^s x^{-s}dx - \int_{\lambda_+}^1(x^2 - \lambda^2 - T_0 x)^s x^{-s}dx\right\}\kappa^2 -$$

$$\int_\kappa^{\lambda_-}(\lambda^2 - x^2 - T_0 x)^s x^{2-s}dx + \int_{\lambda_+}^1(x^2 - \lambda^2 - T_0 x)^s x^{2-s}dx$$

$$0 = \int_\kappa^{\lambda_-}(\lambda^2 - x^2 - T_0 x)^s x^{-s}dx - \int_{\lambda_+}^1(x^2 - \lambda^2 - T_0 x)^s x^{-s}dx, \quad (3)$$

$$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1-\kappa^2}.$$

In the viscosity measuring apparatus according to the present invention, the first relative movement distance $\Delta L_1$ and the second relative movement distance $\Delta L_2$ may be smaller than the initial depth $L_0$.

In the viscosity measuring apparatus according to the present invention, before the control unit obtains the flow behavior index n, the control unit may be configured to judge whether the convergent value $F_{Te}$ of the force applied to the plunger from the sample at the first relative movement velocity $v_{p1}$ or the second relative movement velocity $v_{p2}$ is larger or not than a buoyancy force $F_b$ applied to the plunger from the sample, and when the control unit judges that the convergent value $F_{Te}$ is larger than the buoyancy force $F_b$, the control unit is configured to perform the process for obtaining the flow behavior index n.

In the viscosity measuring apparatus according to the present invention, the relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; the plunger ratio $\kappa$; and the flow behavior index n of the sample may include the above Expressions (2) to (5) and the following Expression (6):

[NO 6]

$$s = \frac{1}{n} = \frac{\ln\left(\frac{v_{p2}/\Phi_2}{v_{p1}/\Phi_1}\right)}{\ln\left(\frac{F_{cb2}/(L_0 + L_{2\_2})\lambda_2^2}{F_{cb1}/(L_0 + L_{2\_1})\lambda_1^2}\right)}. \quad (6)$$

In the viscosity measuring apparatus according to the present invention, when the control unit obtains the flow behavior index n, the control unit may be configured:

to determine a provisional flow behavior index $n_a$;

to obtain, based on the above Expressions (3) to (5) established among: the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio $\kappa$; and a first dimensionless coordinate $\lambda_1$; or based on a graph or a table created based on the above Expressions (3) to (5), the first dimensionless coordinate $\lambda_1$;

to obtain, based on the above Expression (2) established among the provisional flow behavior index $n_a$, the first dimensionless coordinate $\lambda_1$ and a first dimensionless flow velocity $\Phi_1$, or based on a graph or a table created based on the above Expression (2), the first dimensionless flow velocity $\Phi_1$;

to obtain, based on the above Expressions (3) to (5) established among: the provisional flow behavior index $n_a$; the second relative movement distance $\Delta L_2$, the second peak value $F_{T2}$ and the second convergent value $F_{Te2}$, at the second relative movement velocity $v_{p2}$; the plunger ratio $\kappa$; and a second dimensionless coordinate $\lambda_2$; or based on a graph or a table created based on the above Expressions (3) to (5), the second dimensionless coordinate $\lambda_2$;

to obtain, based on the above Expression (2) established among the provisional flow behavior index $n_a$, the second dimensionless coordinate $\lambda_2$ and a second dimensionless flow velocity $\Phi_2$, or based on a graph or a table created based on the above Expression (2), the second dimensionless flow velocity $\Phi_2$;

to obtain a flow behavior index n based on: the first dimensionless coordinate $\lambda_1$ and the first dimensionless flow velocity $\Phi_1$ at the first relative movement velocity $v_{p1}$; the second dimensionless coordinate $\lambda_2$ and the second dimensionless flow velocity $\Phi_2$ at the second relative movement velocity $v_{p2}$; and the above Expression (6); and to return to the step of determining a provisional flow behavior index $n_a$, when the control unit compares the obtained flow behavior index n to the provisional flow behavior index $n_a$ to find out that the obtained flow behavior index n is different from the provisional flow behavior index $n_a$.

A viscosity measuring apparatus according to the present invention is a viscosity measuring apparatus comprising:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container;

a measuring unit disposed on the plunger and configured to measure a force applied to the plunger from the sample; and a control unit configured to control the driving unit; wherein:

the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a relative movement distance $\Delta L$;

the measuring unit is configured to measure a force applied to the plunger from the sample with a passage of time, during the further immersing operation of the plunger at the first relative movement velocity $v_{p1}$ and after the further immersing operation thereof;

the control unit is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by the relative movement distance $\Delta L$;

the measuring unit is configured to measure a force applied to the plunger from the sample with a passage of time, during the further immersing operation of the plunger at the second relative movement velocity $v_{p2}$ and after the further immersing operation thereof;

the control unit is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control unit is further configured to obtain, based on a predetermined relationship established among: the first peak value $F_{T1}$ and the first convergent value $F_{Te1}$, at the first relative movement velocity $v_{p1}$; the second peak value $F_{T2}$ and the second convergent value $F_{Te2}$, at the second relative movement velocity $v_{p2}$; the relative movement distance $\Delta L$; a plunger ratio $\kappa = R_i/R_0$; and a flow behavior index n of the sample; the flow behavior index n; and the control unit is further configured, when the first relative movement velocity $v_{p1}$ is represented as $v_p$, the first peak value $F_{T1}$ is represented as $F_T$, and the first convergent value $F_{Te1}$ is represented as $F_{Te}$, or when the second relative movement velocity $v_{p2}$ is represented as $v_p$, the second peak value $F_{T2}$ is represented as $F_T$, and the second convergent value $F_{Te2}$ is represented as $F_{Te}$, to calculate an apparent viscosity $\mu_a$ of the sample based on the $v_p$, the $F_T$, the $F_{Te}$, the relative movement distance $\Delta L$, the plunger ratio $\kappa$, the flow behavior index n, a density $\rho$ of the sample, a gravitational acceleration g, and the following Expression (1):

[NO 7]

$$\mu_a = \frac{\sigma_w}{d\gamma/dt} = \frac{\sigma_0 + K\left(\frac{d\gamma}{dt}\right)^n}{d\gamma/dt} \tag{1}$$

in which $$\sigma_w = \frac{T_w PR_0}{2}, \frac{d\gamma}{dt} = \left(\frac{\lambda^2}{\kappa} - \kappa - T_0\right)^s \left(\frac{PR_0}{2K}\right)^s, \tag{2}$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx\right\}\kappa^2 -$$

$$\int_\kappa^{\lambda_-} (\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx, \tag{3}$$

$$s = \frac{1}{n}, \lambda_- = \frac{1}{2}\left[(T_0^2 + 4\lambda^2)^{\frac{1}{2}} - T_0\right], \tag{4}$$

$$\lambda_+ = \frac{1}{2}\left[(T_0^2 + 4\lambda^2)^{\frac{1}{2}} + T_0\right], \tag{5}$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

In addition, a viscosity measuring apparatus according to the present invention is a viscosity measuring apparatus comprising:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container;

a measuring unit disposed on the plunger and configured to measure a force applied to the plunger from the sample; and a control unit configured to control the driving unit; wherein:

the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control unit is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control unit is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control unit is further configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n;

the control unit is further configured to control the driving unit such that the plunger is returned coaxially with the cylindrical container to the initial depth $L_0$ and stopped thereat, and that the plunger is then further immersed into the sample coaxially with the cylindrical container at a third relative movement velocity $v_{p3}$ by a third relative movement distance $\Delta L_3$;

the measuring unit is configured to measure a force applied to the plunger from the sample with a passage of time, during the further immersing operation of the plunger at the third relative movement velocity $v_{p3}$ and after the further immersing operation thereof;

the control unit is configured to obtain a third peak value $F_{T3}$ and a third convergent value $F_{Te3}$ of the force applied to the plunger from the sample, based on measured values of the force caused by the relative movement of the plunger at the third relative movement velocity $v_{p3}$; and the control unit is further configured to calculate, when the third relative movement velocity $v_{p3}$ is represented as $v_p$, the third relative movement distance $\Delta L_3$ is represented as $\Delta L$, the third peak value $F_{T3}$ is represented as $F_T$ and the third convergent value $F_{Te3}$ is represented as $F_{Te}$, an apparent viscosity $\mu_a$ of the sample based on the $v_p$, the $\Delta L$, the $F_T$ and the $F_{Te}$, the plunger ratio $\kappa$, the flow behavior index n, a density $\rho$ of the sample, a gravitational acceleration g, and the following Expression (1):

[NO 8]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w P R_0}{2}, \frac{d\gamma}{dt} = \left(\frac{\lambda^2}{\kappa} - \kappa - T_0\right)^s \left(\frac{P R_0}{2K}\right)^s, \quad (2)$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_{\kappa}^{\lambda_-}(\lambda^2 - x^2 - T_0 x)^s x^{-s} dx - \int_{\lambda_+}^{1}(x^2 - \lambda^2 - T_0 x)^s x^{-s} dx\right\}\kappa^2 -$$

$$\int_{\kappa}^{\lambda_-}(\lambda^2 - x^2 - T_0 x)^s x^{2-s} dx + \int_{\lambda_+}^{1}(x^2 - \lambda^2 - T_0 x)^s x^{2-s} dx$$

-continued $$0 = \int_{\kappa}^{\lambda_-}(\lambda^2 - x^2 - T_0 x)^s x^{-s} dx - \int_{\lambda_+}^{1}(x^2 - \lambda^2 - T_0 x)^s x^{-s} dx, \quad (3)$$

$$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

A control apparatus according to the present invention is a control apparatus for controlling a viscosity measuring apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container; and a measuring unit disposed on the plunger and configured to measure a force applied to the plunger from the sample;

wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control apparatus is further configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n;

the control apparatus is further configured to calculate, when the first relative movement velocity $v_{p1}$ is represented as $v_p$, the first relative movement distance $\Delta L_1$ is represented as $\Delta L$, the first peak value $F_{T1}$ is represented as $F_T$, and the first convergent value $F_{Te1}$ is represented as $F_{Te}$, or when the second relative movement velocity $v_{p2}$ is represented as $v_p$, the second relative movement distance $\Delta L_2$ is represented as $\Delta L$, the second peak value $F_{T2}$ is represented as $F_T$, and the second convergent value $F_{Te2}$ is represented as $F_{Te}$, an apparent viscosity $\mu_a$ of the sample based on the $v_p$, the $\Delta L$, the $F_T$, the $F_{Te}$, the plunger ratio $\kappa$, the flow behavior index n, a density $\rho$ of the sample, a gravitational acceleration g, and the following Expression (1):

[NO 9]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w P R_0}{2}, \frac{d\gamma}{dt} = \left(\frac{\lambda^2}{\kappa} - \kappa - T_0\right)^s \left(\frac{PR_0}{2K}\right)^s, \quad (2)$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{ \int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx \right\} \kappa^2 -$$

$$\int_\kappa^{\lambda_-} (\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx, \quad (3)$$

$$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i (L_0 + L_2)}, F_y = F_{Te} - F_b,$$

$$F_{cb} = F_T - F_b, F_b = \pi R_i^2 L_2 \rho g, L_2 = \frac{\Delta L}{1-\kappa^2}.$$

In the control apparatus according to the present invention, the first relative movement distance $\Delta L_1$ and the second relative movement distance $\Delta L_2$ may be smaller than the initial depth $L_0$.

In the control apparatus according to the present invention, the control apparatus may be configured to judge, before the control apparatus obtains the flow behavior index n, whether the convergent value $F_{Te}$ of the force applied to the plunger from the sample at the first relative movement velocity $v_{p1}$ or the second relative movement velocity $v_{p2}$ is larger or not than a buoyancy force $F_b$ applied to the plunger from the sample, and configured to perform the process for obtaining the flow behavior index n, when the control apparatus judges that the convergent value $F_{Te}$ is larger than the buoyancy force $F_b$.

In the control apparatus according to the present invention, the relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; the plunger ratio $\kappa$; and the flow behavior index n of the sample may include the above Expressions (2) to (5) and the following Expression (6):

[数 10]

$$s = \frac{1}{n} = \frac{\ln\left(\frac{v_{p2}/\Phi_2}{v_{p1}/\Phi_1}\right)}{\ln\left(\frac{F_{cb2}/(L_0 + L_{2\_2})\lambda_2^2}{F_{cb1}/(L_0 + L_{2\_1})\lambda_1^2}\right)}. \quad (6)$$

In the control apparatus according to the present invention, when the control apparatus obtains the flow behavior index n, the control apparatus may be configured:

to determine a provisional flow behavior index $n_a$;

to obtain, based on the above Expressions (3) to (5) established among: the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio $\kappa$; and a first dimensionless coordinate $\lambda_1$; or based on a graph or a table created based on the above Expressions (3) to (5), the first dimensionless coordinate $\lambda_1$;

to obtain, based on the above Expression (2) established among the provisional flow behavior index $n_a$, the first dimensionless coordinate $\lambda_1$ and a first dimensionless flow velocity $\Phi_1$, or based on a graph or a table created based on the above Expression (2), the first dimensionless flow velocity $\Phi_1$;

to obtain, based on the above Expressions (3) to (5) established among: the provisional flow behavior index $n_a$; the second relative movement distance $\Delta L_2$, the second peak value $F_{T2}$ and the second convergent value $F_{Te2}$, at the second relative movement velocity $v_{p2}$; the plunger ratio $\kappa$; and a second dimensionless coordinate $\lambda_2$; or based on a graph or a table created based on the above Expressions (3) to (5), the second dimensionless coordinate $\lambda_2$;

to obtain, based on the above Expression (2) established among the provisional flow behavior index $n_a$, the second dimensionless coordinate $\lambda_2$ and a second dimensionless flow velocity $\Phi_2$, or based on a graph or a table created based on the above Expression (2), the second dimensionless flow velocity $\Phi_2$;

to obtain a flow behavior index n based on: the first dimensionless coordinate $\lambda_1$ and the first dimensionless flow velocity $\Phi_1$ at the first relative movement velocity $v_{p1}$; the second dimensionless coordinate $\lambda_2$ and the second dimensionless flow velocity $\Phi_2$ at the second relative movement velocity $v_{p2}$; and the above Expression (6); and to return to the step of determining a provisional flow behavior index $n_a$, when the control apparatus compares the obtained flow behavior index n to the provisional flow behavior index $n_a$ to find out that the obtained flow behavior index n is different from the provisional flow behavior index $n_a$.

A control apparatus according to the present invention is a control apparatus for controlling a viscosity measuring apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container; and a measuring unit disposed on the plunger and configured to measure a force applied to the plunger from the sample; wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a relative movement distance $\Delta L$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by the relative movement distance $\Delta L$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control apparatus is further configured to obtain, based on a predetermined relationship established among: the first peak value $F_{T1}$ and the first convergent value $F_{Te1}$, at the first relative movement velocity $v_{p1}$; the second peak value $F_{T2}$ and the second convergent value $F_{Te2}$, at the second relative movement velocity $v_{p2}$; the relative movement distance $\Delta L$; a plunger ratio $\kappa = R_i/R_0$; and a flow behavior index n of the sample; the flow behavior index n; and the control apparatus is further configured to calculate, when the first relative movement velocity $v_{p1}$ is represented as $v_p$, the first peak value $F_{T1}$ is represented as $F_T$, and the first convergent value $F_{Te1}$ is represented as $F_{Te}$, or when the second relative movement velocity $v_{p2}$ is represented as $v_p$, the second peak value $F_{T2}$ is represented as $F_T$, and the second convergent value $F_{Te2}$ is represented as $F_{Te}$, an apparent viscosity $\mu_a$ of the sample based on the $v_p$, the $F_T$, the $F_{Te}$, the relative movement distance $\Delta L$, the plunger ratio $\kappa$, the flow behavior index n, a density $\rho$ of the sample, a gravitational acceleration g, and the following Expression (1):

[NO 11]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w P R_0}{2}, \frac{d\gamma}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_\kappa^{\lambda_-} (\lambda^2 - x^2 - T_0 x)^s x^{-s} dx - \int_{\lambda_+}^{1} (x^2 - \lambda^2 - T_0 x)^s x^{-s} dx\right\} \kappa^2 - \quad (2)$$

$$\int_\kappa^{\lambda_-} (\lambda^2 - x^2 - T_0 x)^s x^{2-s} dx + \int_{\lambda_+}^{1} (x^2 - \lambda^2 - T_0 x)^s x^{2-s} dx$$

$$0 = \int_\kappa^{\lambda_-} (\lambda^2 - x^2 - T_0 x)^s x^{-s} dx - \int_{\lambda_+}^{1} (x^2 - \lambda^2 - T_0 x)^s x^{-s} dx, \quad (3)$$

$$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

In addition, a control apparatus according to the present invention is a control apparatus for controlling a viscosity measuring apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container; and a measuring unit disposed on the plunger and configured to measure a force applied to the plunger from the sample; wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control apparatus is further configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a third relative movement velocity $v_{p3}$ by a third relative movement distance $\Delta L_3$;

the measuring unit is configured to measure a force applied to the plunger from the sample with a passage of time, during the further immersing operation of the plunger at the third relative movement velocity $v_{p3}$ and after the further immersing operation thereof;

the control apparatus is configured to obtain a third peak value $F_{T3}$ and a third convergent value $F_{Te1}$ of the force applied to the plunger from the sample, based on measured values of the force caused by the relative movement of the plunger at the third relative movement velocity $v_{p3}$; and the control apparatus is further configured to calculate, when the third relative movement velocity $v_{p3}$ is represented as $v_p$, the third relative movement distance $\Delta L_3$ is represented as $\Delta L$, the third peak value $F_{T3}$ is represented as $F_T$ and the third convergent value $F_{Te3}$ is represented as $F_{Te}$, an apparent viscosity $\mu_a$ of the sample based on the $v_p$, the $\Delta L$, the $F_T$ and the $F_{Te}$, the plunger ratio $\kappa$, the flow behavior index n, a density $\rho$ of the sample, a gravitational acceleration g, and the following Expression (1):

[NO 12]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w P R_0}{2}, \frac{d\gamma}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

-continued $$\Phi = \left\{ \int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx \right\} \kappa^2 - \int_\kappa^{\lambda_-} (\lambda^2 - x^2 - T_0 x)^s x^{2-s} dx + \int_{\lambda_+}^1 (x^2 - \lambda^2 - T_0 x)^s x^{2-s} dx \quad (2)$$

$$0 = \int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx, \quad (3)$$

$$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i (L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

The control apparatus or the respective elements of the control apparatus may be realized by a computer system.

In addition, the present invention also covers a program executed by a computer system for realizing the control apparatus or the respective elements of the control apparatus, and a computer-readable storage medium storing the program.

Herein, the storage medium includes not only a flexible disc that can be recognized as itself, but also a network transmitting various signals.

According to the present invention, an apparent viscosity of a sample of a non-Newtonian fluid can be precisely measured.

DESCRIPTION OF THE PREFERRED EMBODIMENT

An embodiment of the present invention will be described in detail below, with reference to the accompanying drawings.

Figure 1:
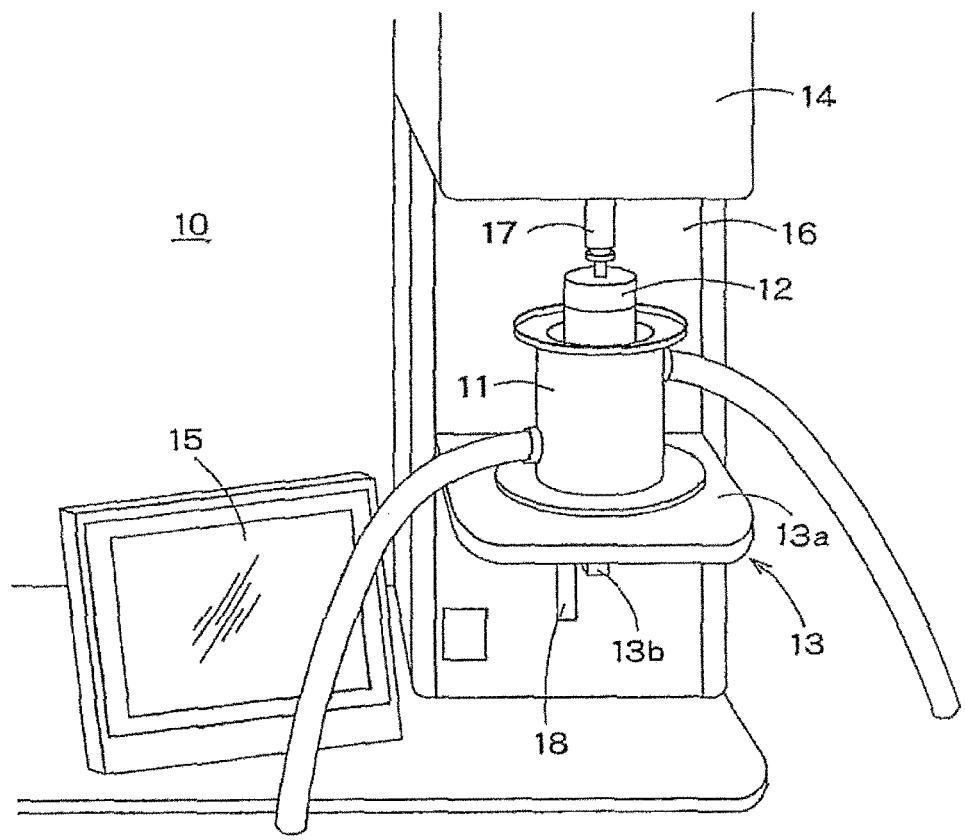
FIG. 1 is a schematic view of a viscosity measuring apparatus in one embodiment of the present invention.
Figure 2:
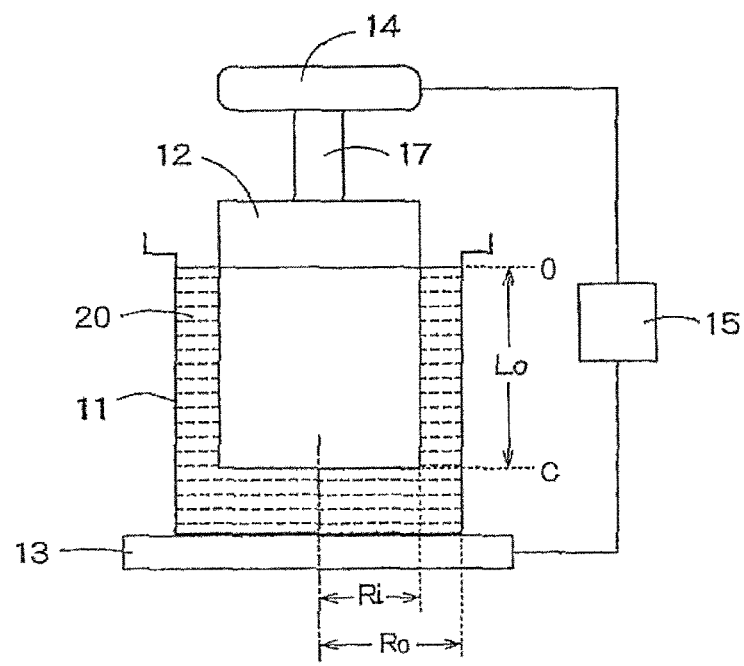
FIG. 2 is a schematic diagram for explaining a structure of the viscosity measuring apparatus of FIG. 1.

FIG. 1 is a schematic view of a viscosity measuring apparatus in one embodiment of the present invention, and FIG. 2 is a schematic diagram for explaining a function of the viscosity measuring apparatus.

As shown in FIGS. 1 and 2, a viscosity measuring apparatus 10 in this embodiment includes: a cylindrical container 11 having a predetermined inner radius $R_0$, in which a sample is contained; a plunger 12 having an outer radius $R_i$ that is smaller than the inner radius $R_0$ of the cylindrical container 11, the plunger 12 being arranged inside the cylindrical container 11 coaxially or concentrically therewith so as to be relatively movable; a driving unit 13 configured to relatively move the plunger 12 coaxially with the cylindrical container 11; a measuring unit 14 configured to measure a force applied to the plunger 12 from the sample; and a control unit (control apparatus) 15 configured to control the driving unit 13.

The driving unit 13 in this embodiment includes: a base seat 13a on which surface the cylindrical container 11 is placed; a support member 13b supporting the base seat 13a; and a ball screw (not shown) configured to linearly move the support member 13b in the vertical direction; and a motor (not shown) connected to the ball screw.

The ball screw and the motor are arranged inside a housing 16 of the viscosity measuring apparatus 10, and illustration of them is omitted. A screw shaft of the ball screw vertically stands in the housing 16.

A vertically extending slit 18 is formed in a front surface of the housing 16. The support member 13b has a horizontally extending elongate shape. One end side of the support member 13b is fixed on a nut portion of the ball screw through the slit 18.

The base seat 13a is fixed on the other end side of the support member 13b, with the surface thereof being oriented vertically upward. The cylindrical container 11 is placed on the surface of the base seat 13a, such that a central axis of the cylindrical container 11 is in parallel with the vertical direction.

The motor (not shown) is configured to transmit a rotating power to the ball screw (not shown). The rotating power transmitted to the ball screw is converted to a vertical linear power, so that the support member 13b is linearly moved in the vertical direction together with the base seat 13a and the cylindrical container 11 on the base seat 13a.

The measuring unit 14 in this embodiment is a load sensor (load cell). The measuring unit 14 is arranged vertically above the base seat 13a, and is supported fixedly to the housing 16. A measuring surface of the measuring unit 14 is oriented vertically downward.

A plunger attachment 17 is fixed on the measuring surface of the measuring unit 14, and the plunger 12 is attached to the plunger attachment 17. Thus, a vertically upward force applied to the plunger 12 is transmitted to the measuring unit 14 through the plunger attachment 17. The measuring unit 14 is configured to measure a value of the force with a passage of time.

The cylindrical container 11 is arranged coaxially with the plunger 12. The outer radius $R_i$ of the plunger 12 is smaller than the inner radius $R_0$ of the cylindrical container 11. Thus, when the cylindrical container 11 is linearly moved vertically upward by the driving unit 13, the plunger 12 is relatively inserted from above into the cylindrical container 11 coaxially therewith in a noncontact manner.

The control unit 15 in this embodiment is connected to the measuring unit 14, and is configured to read out a measurement value of the force measured by the measuring unit 14 and to store the measurement value in a storage unit. The control unit 15 is formed of a computer system including the storage unit storing a control program and so on.

In addition, the control unit 15 is connected to the driving unit 13 so as to control an operation of the driving unit 13. To be specific, the control unit 15 is connected to the motor of the driving unit 13 so as to control a direction and a value of a current to be supplied to the motor, whereby a rotating direction and a rotating amount of the motor are controlled. As a result, the cylindrical container 11 on the base seat 13a is linearly moved vertically upward at a desired velocity, and is located (stopped) at a desired position in the vertical direction.

Further, the control unit 15 in this embodiment is configured to control the driving unit 13 such that the plunger 12 is immersed into the sample 20 contained in the cylindrical container 11 coaxially with the cylindrical container 11 by a predetermined initial depth $L_0$ and stopped thereat, and that the plunger 12 is then further immersed into the sample 20 coaxially with the cylindrical container 11 at a first relative movement velocity $v_{p1}$ by a first relative movement distance $\Delta L_1$. During the further immersing operation of the plunger 12 at the first relative movement velocity $v_{p1}$ and after the further immersing operation thereof, the measurement unit 14 in this embodiment is configured to measure a force applied to the plunger 12 from the sample 20 with a passage of time. The control unit 15 in this embodiment is configured to obtain a first peak value $F_{T1}$ and a first convergent value $F_{Te1}$ of the force applied to the plunger 12 from the sample 20, based on measurement values of the force caused by the relative movement of the plunger 12 at the first relative movement velocity $v_{p1}$.

Further, the control unit 15 in this embodiment is configured to control the driving unit 13 such that the plunger 12 is returned coaxially with the cylindrical container 11 to the initial depth $L_0$ and stopped thereat, and that the plunger 12 is then further immersed into the sample 20 at a second relative movement velocity $v_{p2}$, which is different from the first relative movement velocity $v_{p1}$, by a predetermined movement distance $\Delta L_2$. During the further immersing operation of the plunger 12 at the second relative movement velocity $v_{p2}$ and after the further immersing operation thereof, the measurement unit 14 in this embodiment is configured to measure a force applied to the plunger 12 from the sample 20 with a passage of time. Then, the control unit 15 in this embodiment is configured to obtain a second peak value $F_{T2}$ and a second convergent value $F_{Te2}$ of the force applied to the plunger 12 from the sample 20, based on measurement values of the force caused by the relative movement of the plunger 12 at the second relative movement velocity $v_{p2}$.

Although not necessary, the control unit 15 in this embodiment is configured to control the driving unit 13 such that the plunger 12 is returned coaxially with the cylindrical container 11 to the initial depth $L_0$ and stopped thereat, and that the plunger 12 is then further immersed into the sample 20 at an $m^{th}$ relative movement velocity $v_{pm}$ (m=3, 4, 5, . . . ) by an $m^{th}$ relative movement distance $\Delta L_m$. During the further immersing operation of the plunger 12 at the $m^{th}$ relative movement velocity $v_{pm}$ and after the further immersing operation thereof, the measurement unit 14 in this embodiment is configured to measure a force applied to the plunger 12 from the sample 20 with a passage of time. Then, the control unit 15 in this embodiment is configured to obtain an $m^{th}$ peak value $F_{Tm}$ and an $m^{th}$ convergent value $F_{Tem}$ of the force applied to the plunger 12 from the sample 20, based on measurement values of the force caused by the relative movement of the plunger 12 at the $m^{th}$ relative movement velocity $v_{pm}$.

In this embodiment, the first, second relative movement distances $\Delta L_1$, $\Delta L_2$ (and the $m^{th}$ relative movement distance $\Delta L_m$) are set smaller than the initial depth $L_0$. Since the annular part between the plunger 12 and the cylindrical container 11 has been filled with the sample 20 before the plunger 12 is pushed thereinto, even when the relative movement distances $\Delta L_1$, $\Delta L_2$ of the plunger are short, a steady flow can be generated in the annular part. In addition, since the relative movement distances $\Delta L_1$, $\Delta L_2$ of the plunger are short, an amount of the sample 20 adhering to the plunger 12 and the container 11 is small, whereby the consecutive measurement is enabled.

Further, the control unit 15 in this embodiment is configured to judge whether the convergent value $F_{Te}$ of the force applied to the plunger 12 from the sample 20 at the first relative movement velocity $v_{p1}$ or the second relative movement velocity $v_{p2}$ (or the $m^{th}$ movement velocity $v_{pm}$) is larger or not than a buoyancy force $F_b$ applied to the plunger 12 from the sample 20.

When the control unit 15 in this embodiment judges that the convergent value $F_{Te}$ is larger than the buoyancy force $F_b$, the control unit 15 is configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; (and the $m^{th}$ relative movement distance $\Delta L_m$, md the $m^{th}$ peak value $F_{Tm}$ and $m^{th}$ convergent value $F_{Tem}$, at the $m^{th}$ relative movement velocity $v_{pm}$;) a plunger ratio $\kappa = R_i/R_0$; and a flow behavior index n of the sample 20; the flow behavior index n.

In a case where the control unit 15 in this embodiment judges that the convergent value $F_{Te}$ is larger than the buoyancy force $F_b$, the control unit 15 is further configured to calculate, when the first relative movement velocity $v_{p1}$ is represented as $v_p$, the first relative movement distance $\Delta L_1$ is represented as $\Delta L$, the first peak value $F_{T1}$ is represented as $F_T$, and the first convergent value $F_{Te1}$ is represented as $F_{Te}$, or when the second relative movement velocity $v_{p2}$ is represented as $v_p$, the second relative movement distance $\Delta L_2$ is represented as $\Delta L$, the second peak value $F_{T2}$ is represented as $F_T$, and the second convergent value $F_{Te2}$ is represented as $F_{Te}$, (or when the $m^{th}$ relative movement velocity $v_{pm}$ is represented as $v_p$, the $m^{th}$ relative movement distance $\Delta L_m$ is represented as $\Delta L$, the $m^{th}$ peak value $F_{Tm}$ is represented as $F_T$, and the $m^{th}$ convergent value $F_{Tem}$ is represented as $F_{Te}$,) an apparent viscosity $\mu_a$ of the sample based on the $v_p$, the $\Delta L$, the $F_T$, the $F_{Te}$, the plunger ratio $\kappa$, the flow behavior index n, a density $\rho$ of the sample, a gravitational acceleration g, and the following Expression (1):

[NO 13]

$$\mu_a = \frac{\sigma_w}{d\gamma/dt} = \frac{\sigma_0 + K\left(\frac{d\gamma}{dt}\right)^n}{d\gamma/dt} \quad (1)$$

in which $$\sigma_w = \frac{T_w PR_0}{2}, \frac{d\gamma}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_{\kappa}^{\lambda_-}(\lambda^2 - x^2 - T_0 x)^s x^{-s}dx - \int_{\lambda_+}^{1}(x^2 - \lambda^2 - T_0 x)^s x^{-s}dx\right\}\kappa^2 - \quad (2)$$

$$\int_{\kappa}^{\lambda_-}(\lambda^2 - x^2 - T_0 x)^s x^{2-s}dx + \int_{\lambda_+}^{1}(x^2 - \lambda^2 - T_0 x)^s x^{2-s}dx$$

$$0 = \int_{\kappa}^{\lambda_-}(\lambda^2 - x^2 - T_0 x)^s x^{-s}dx - \int_{\lambda_+}^{1}(x^2 - \lambda^2 - T_0 x)^s x^{-s}dx, \quad (3)$$

$$s = \frac{1}{n}, \lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

The relationship which is used in the process for obtaining the flow behavior index n and established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; the plunger ratio $\kappa$; and the flow behavior index n of the sample specifically includes, for example, the above Expressions (2) to (5) and the following Expression (6):

[NO 14]

$$s = \frac{1}{n} = \frac{\ln\left(\frac{v_{p2}/\Phi_2}{v_{p1}/\Phi_1}\right)}{\ln\left(\frac{F_{cb2}/(L_0 + L_{2\_2})\lambda_2^2}{F_{cb1}/(L_0 + L_{2\_1})\lambda_1^2}\right)}. \quad (6)$$

Specifically, for example, when the control unit 15 obtains the flow behavior index n, the control unit 15 is configured:

to determine a provisional flow behavior index $n_a$;

to obtain, based on the above Expressions (3) to (5) established among: the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio $\kappa$; and a first dimensionless coordinate $\lambda_1$; or based on a graph or a table created based on the above Expressions (3) to (5), the first dimensionless coordinate $\lambda_1$;

to obtain, based on the above Expression (2) established among the provisional flow behavior index $n_a$, the first dimensionless coordinate $\lambda_1$ and a first dimensionless flow velocity $\Phi_1$, or based on a graph or a table created based on the above Expression (2), the first dimensionless flow velocity $\Phi_1$;

to obtain, based on the above Expressions (3) to (5) established among: the provisional flow behavior index $n_a$; the second relative movement distance $\Delta L_2$, the second peak value $F_{T2}$ and the second convergent value $F_{Te2}$, at the second relative movement velocity $v_{p2}$; the plunger ratio $\kappa$; and a second dimensionless coordinate $\lambda_2$; or based on a graph or a table created based on the above Expressions (3) to (5), the second dimensionless coordinate $\lambda_2$;

to obtain, based on the above Expression (2) established among the provisional flow behavior index $n_a$, the second dimensionless coordinate $\lambda_2$ and a second dimensionless flow velocity $\Phi_2$, or based on a graph or a table created based on the above Expression (2), the second dimensionless flow velocity $\Phi_2$;

to obtain a flow behavior index n based on: the first dimensionless coordinate $\lambda_1$ and the first dimensionless flow velocity $\Phi_1$ at the first relative movement velocity $v_{p1}$; the second dimensionless coordinate $\lambda_2$ and the second dimensionless flow velocity $\Phi_2$ at the second relative movement velocity $v_{p2}$; and the above Expression (6); and to proceed on to the process for calculating an apparent viscosity $\mu_a$ of the sample, when the control unit 15 compares the obtained flow behavior index n to the provisional flow behavior index $n_a$ to find out that the obtained flow behavior index n is equal to the provisional flow behavior index $n_a$, or to return to the step of determining a provisional flow behavior index $n_a$, when the control unit 15 compares the obtained flow behavior index n to the provisional flow behavior index $n_a$ to find out that the obtained flow behavior index n is different from the provisional flow behavior index $n_a$.

In this specification, the term "equal" is not limited to a strict meaning, and is construed to include values within a measurement error.

When the dimensionless coordinates are obtained by calculation based on the above Expressions (3) to (5), a numerical analysis program capable of doing an approximate calculation by the Simpson method can be used. On the other hand, when the dimensionless coordinates are obtained based on a graph or a table created based on the above Expressions (3) to (5), methods described in, for example, Fredrickson, A., Bird, R. B., Non-Newtonian flow in annuli. Industrial & Engineering Chemistry, 50, 347-352 (1958), or Hanks, R. W. "The Axial Laminar Flow of Yield-Pseudoplastic Fluids in a Concentric Annular part". Ind. Eng. Chem. Process Des. Dev., 18(3), 488-493. (1979) can be utilized. In addition, when the dimensionless flow velocities are obtained based on a graph or a table created based on the above Expression (2), a method described in, for example, the aforementioned Non-Patent Document 3 can be utilized.

When the control unit 15 in this embodiment judges whether the convergent value $F_{Te}$ of the force applied to the plunger 12 from the sample 20 at the first relative movement velocity $v_{p1}$ or the second relative movement velocity $v_{p2}$ (or the $m^{th}$ relative movement velocity $v_{pm}$) is larger or not than a buoyancy force $F_b$ applied to the plunger 12 from the sample 20 to find out that the convergent value $F_{Te}$ is equal to the buoyancy force $F_b$, the control unit 15 is configured to obtain an inverse s (=1/n) of the flow behavior index n of the sample 20 based on the first relative movement distance $\Delta L_1$ and the first peak value $F_{T1}$ at the first relative movement velocity $v_{p1}$, the second relative movement distance $\Delta L_2$ and the second peak value $F_{T2}$ at the second relative movement velocity $v_{p2}$, (and the $m^{th}$ relative movement distance $\Delta L_m$ and the $m^{th}$ peak value $F_{Tm}$ at the $m^{th}$ relative movement velocity $v_{pm}$,) and the following Expression (8):

[NO 15]

$$s = \frac{1}{n} = \frac{\ln(v_{p2}/v_{p1})}{\ln\left[\left(\frac{F_{cb2}}{L_0 + L_{2\_2}}\right)/\left(\frac{F_{cb1}}{L_0 + L_{2\_1}}\right)\right]}. \tag{8}$$

When the control unit 15 in this embodiment judges whether or not the obtained flow behavior index n is equal to 1 or not to find out that the flow behavior index n is equal to 1, the control unit 15 is configured to calculate a viscosity of the sample 20 based on the viscosity measuring method described in the Patent Document 1 (JP2014-055928A). On the other hand, when the flow behavior index n is different from 1, the control unit 15 is configured to calculate an apparent viscosity of the sample 20 based on the viscosity measuring method described in the Patent Document 2 (JP5596244B).

Next, an operation of the above embodiment is described.

Firstly, the cylindrical container 11 containing the non-Newtonian fluid sample 20 is placed on a surface of the base seat 13a such that the cylindrical container 11 is coaxially positioned with the plunger 12.

Figure 3:
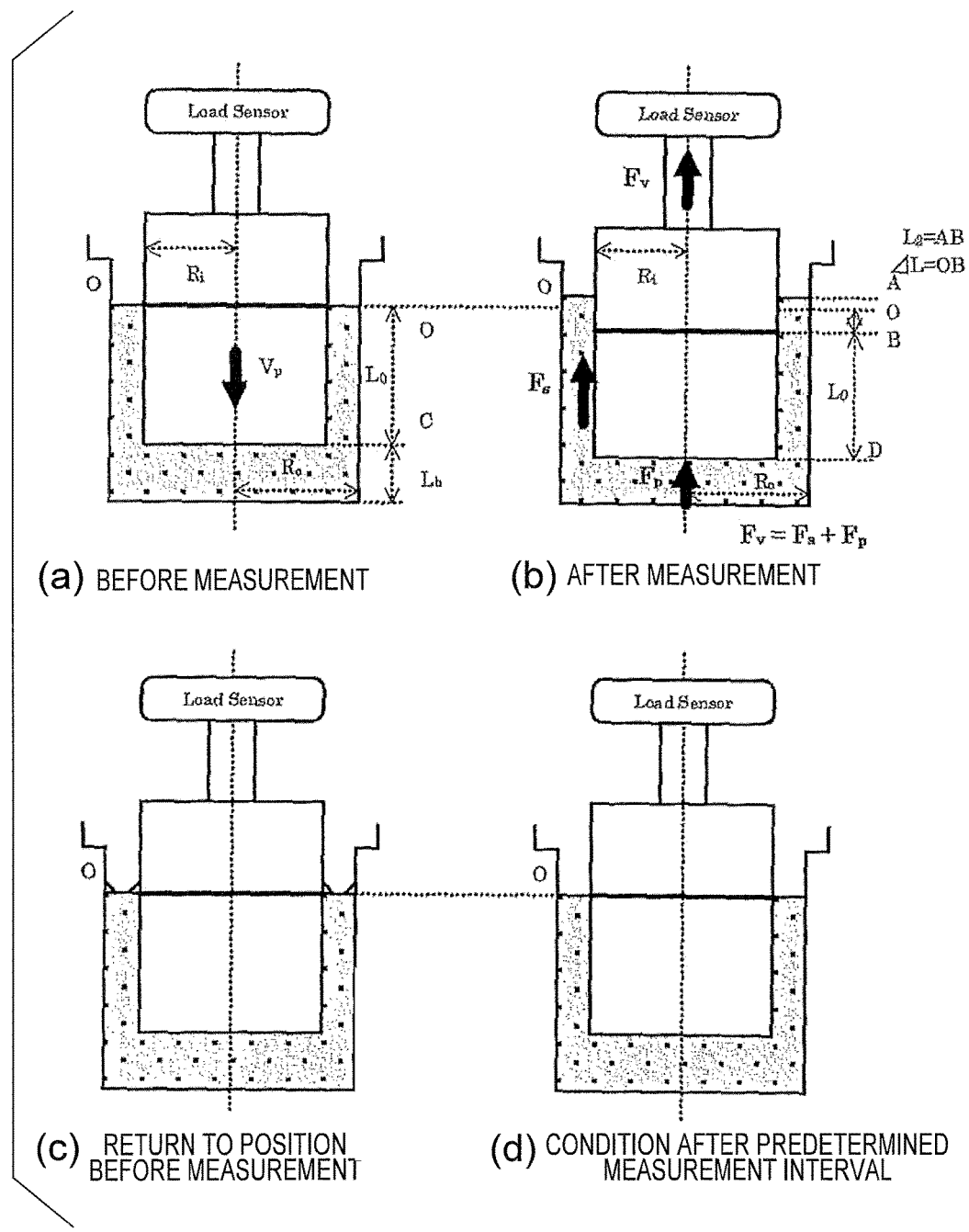
FIG. 3 is a view for explaining an operation of the viscosity measuring apparatus in the SBE method.

(A) Then, the driving unit 13 is controlled by the control unit 15 such that the cylindrical container 11 is linearly moved vertically upward whereby a lower end of the plunger 12 is immersed into the sample 20 in the cylindrical container 11 by a predetermined initial depth $L_0$ and stopped thereat (see FIG. 3(a)). Here, a measurement value of the force measured by the measuring unit 14 is initialized to zero.

(B) Then, the driving unit 13 is controlled by the control unit 15 such that the cylindrical container 11 is further linearly moved vertically upward at a first relative movement velocity $v_{p1}$ by a first relative movement distance $\Delta L_1$. Namely, the plunger 12 is further immersed into the sample 20 in the cylindrical container 11 at the first relative movement velocity $v_{p1}$ by the first relative movement distance $\Delta L_1$ (see FIG. 3(b)).

Figure 5:
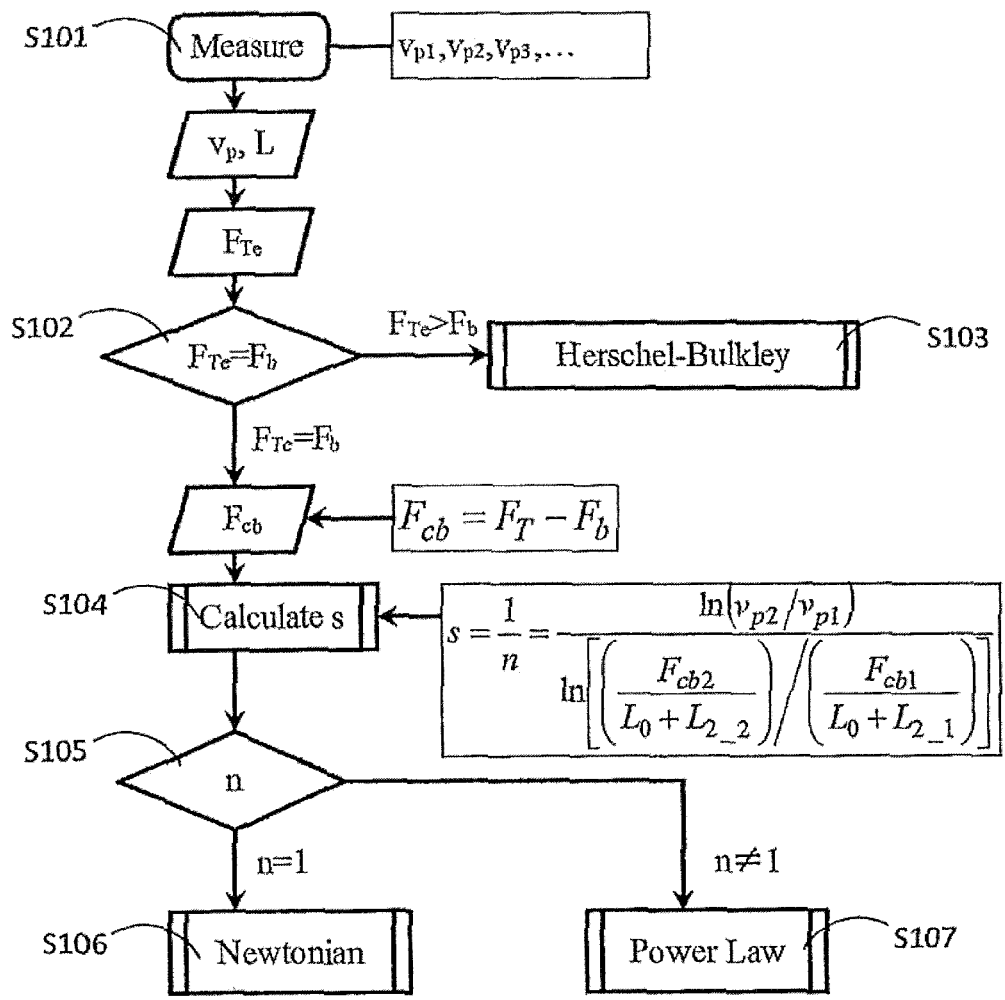
FIG. 5 is a flowchart for explaining a viscosity measuring method according to one embodiment of the present invention.

During the further immersing operation of the plunger 12 at the first relative movement velocity $v_{p1}$ and after the further immersing operation thereof, a vertically upward force applied to the plunger 12 from the sample 20 is measured by the measuring unit 14 with a passage of time (see step S101 in FIG. 5). Measured values of the force measured by the measuring unit 14 are read out by the control unit 15 and stored.

Figure 4:
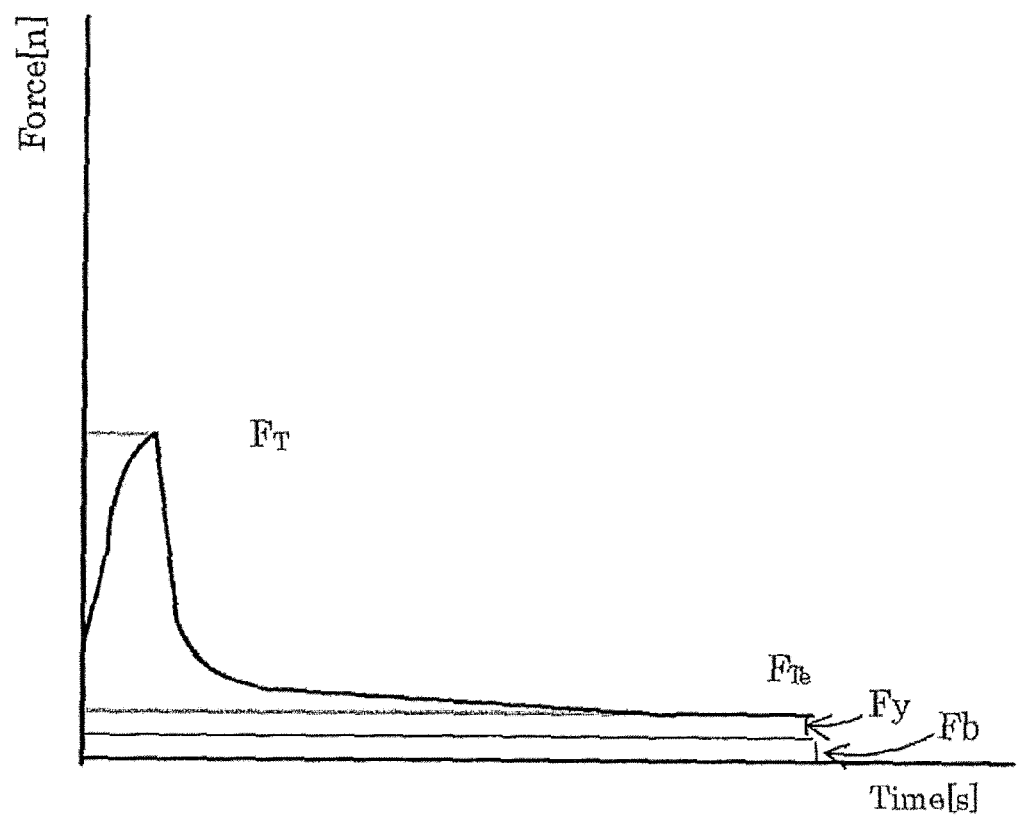
FIG. 4 is graph showing an example of a force-time curve created by one embodiment of the present invention.

(C) The control unit 15 in this embodiment is configured to obtain a first peak value $F_{T1}$ and a first convergent value $F_{Te1}$ of the force applied to the plunger 12 from the sample 20, based on the measurement values of the force caused by the relative movement of the plunger 12 at the first relative movement velocity $v_{p1}$. To be specific, a force-time curve as shown in FIG. 4 is created based on the measured values of the measuring unit 14, and a maximum value of the force-time curve is taken as the first peak value $F_{T1}$. In addition, a value corresponding to a value when sample is left for a predetermined period of time (e.g., about 5 to 30 minutes) is calculated from a convergent curve of the force-time curve, and is taken as the first convergent value $F_{Te1}$. According to a result of the experiment conducted by the inventor, a time corresponding to the maximum value (peak value) of the force-time curve is often in conformity to a moment at which the further immersing operation is stopped, but is sometimes before the moment at which the further immersing operation is stopped.

(D) Then, the driving unit 13 is controlled by the control unit 15 such that the cylindrical container 11 is linearly moved vertically downward whereby the plunger 12 is returned coaxially with the cylindrical container 11 to the initial depth $L_0$ and stopped thereat. In this embodiment, since the relative movement distance of the plunger 12 is short, an amount of the sample 20 adhering to the container 11 and the plunger 12 is slight (see FIG. 3(c)). Thus, a measurement interval required for a liquid level of the sample 20 to be settled can be shortened (see FIG. 3(d)).

(E) Then, the driving unit 13 is controlled by the control unit 15 such that the cylindrical container 11 is linearly moved vertically upward at a second relative movement velocity $v_{p2}$ by a second relative movement distance $\Delta L_2$ which is different from the first relative movement distance $\Delta L_1$. Namely, the plunger 12 is further immersed into the sample 20 in the cylindrical container 11 at the second relative movement velocity $v_{p2}$ by the second relative movement distance $\Delta L_2$.

During the further immersing operation of the plunger 12 at the second relative movement velocity $v_{p2}$ and after the further immersing operation thereof, a vertically upward force applied to the plunger 12 from the sample 20 is measured by the measuring unit 14 with a passage of time (see step S101 in FIG. 5). Measured values of the force measured by the measuring unit 14 are read out by the control unit 15 and stored.

The control unit 15 in this embodiment is configured to obtain a second peak value $F_{T2}$ and a second convergent value $F_{Te2}$ of the force applied to the plunger 12 from the sample 20, based on the measurement values of the force caused by the relative movement of the plunger 12 at the second relative movement velocity $v_{p2}$. To be specific, a force-time curve is created based on the measured values of the measuring unit 14, and a maximum value of the force-time curve is taken as the second peak value $F_{T2}$. In addition, a value corresponding to a value when sample is left for a predetermined period of time (e.g., about 5 to 30 minutes) is calculated from a convergent curve of the force-time curve, and is taken as the second convergent value $F_{Te2}$.

Both of the first and second relative movement distances $\Delta L_1$ and $\Delta L_2$ of the plunger 12 are values at which a steady flow can be obtained in the annular part between the plunger 12 and the cylindrical container 11. In this embodiment, since the annular part is filled with the sample 20 before the plunger 12 is relatively moved, a steady flow can be generated in the annular part even when the first and second relative movement distances $\Delta L_1$ and $\Delta L_2$ of the plunger 12 are short. Thus, an amount of the sample 20 adhering to the plunger 12 and to the cylindrical container 11 is small, whereby continuous measurements can be carried out without increasing a measurement error.

Further, by sequentially repeating the step (D), the step (E) in which at least the relative movement velocity of the plunger 12 are changed and the step (F), peak values of forces at three kinds or more relative movement velocities may be respectively obtained. Namely, the driving unit 13 is controlled by the control unit 15 such that the cylindrical container 11 is linearly moved vertically downward, whereby the plunger 12 is returned coaxially with the cylindrical container 11 to the initial depth $L_0$ and stopped thereat. Then, the driving unit 13 is controlled by the control unit 15 such that the cylindrical container 11 is further linearly moved vertically upward at a different $m^{th}$ relative movement velocity $v_{pm}$ (m=3, 4, 5, ...) by an $m^{th}$ relative movement distance $\Delta L_m$. Namely, the plunger 12 is further immersed into the sample 20 in the cylindrical container 11 at the $m^{th}$ relative movement velocity $v_{pm}$ by the $m^{th}$ relative movement distance $\Delta L_m$. During the further immersing operation of the plunger 12 at the $m^{th}$ relative movement velocity $v_{pm}$ and after the further immersing operation thereof, a vertically upward force applied to the plunger 12 from the sample 20 is measured by the measuring unit 14 with a passage of time (see step S101 in FIG. 5). Measurement values of the force measured by the measuring unit 14 are read out by the control unit 15 and stored. The control unit 15 in this embodiment is configured to obtain an $m^{th}$ peak value $F_{Tm}$ and an $m^{th}$ convergent value $F_{Tem}$ of the force applied to the plunger 12 from the sample 20, based on the measurement values of the force caused by the relative movement of the plunger 12 at the $m^{th}$ relative movement velocity $v_{pm}$. To be specific, a force-time curve is created based on the measured values of the measuring unit 14, and a maximum value of the force-time curve is taken as the $m^{th}$ peak value $F_{Tm}$. In addition, a value corresponding to a value when sample is left for a predetermined period of time (e.g., about 5 to 30 minutes) is calculated from a convergent curve of the force-time curve, and is taken as the $m^{th}$ convergent value $F_{Tem}$.

(G) Then, the control unit 15 judges whether the convergent value $F_{Te}$ of the force applied to the plunger 12 from the sample 20 at the first relative movement velocity $v_{p1}$ or the second relative movement velocity $v_{p2}$ (or the $m^{th}$ relative movement velocity $v_{pm}$) is larger or not than a buoyancy force $F_b$ applied to the plunger from the sample (see step S102 in FIG. 5).

When the convergent value $F_{Te}$ is judged to be larger than the buoyancy force $F_b$, the control unit 15 judges that the sample 20 belongs to a Herschel-Bulkley fluid category of non-Newtonian fluids, and applies thereto an analysis method for Herschel-Bulkley fluid (see step S103 in FIG. 5). Namely, the control unit 15 obtains a fluid behavior index n based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; (the $m^{th}$ relative movement distance $\Delta L_m$, the $m^{th}$ peak value $F_{Tm}$ and the $m^{th}$ convergent value $F_{Tem}$, at the $m^{th}$ relative movement velocity $v_{pm}$;) a plunger ratio $\kappa = R_i/R_0$, and a flow behavior index n of the sample 20; i.e., based on the above Expressions (2) to (5) and the below Expression (6).

To be specific, for example, the control unit 15 determines a provisional flow behavior index $n_a$.

Then, a first dimensionless coordinate $\lambda_1$ is obtained based on the above Expressions (3) to (5) established among: the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio $\kappa$; and the first dimensionless coordinate $\lambda_1$; or based on a graph or a table created based on the above Expressions (3) to (5).

Following thereto, a first dimensionless flow velocity $\Phi_1$ is obtained based on the above Expression (2) established among the provisional flow behavior index $n_a$, the obtained first dimensionless coordinate $\lambda_1$ and a first dimensionless flow velocity $\Phi_1$, or based on a graph or a table created based on the above Expression (2).

Then, a second dimensionless coordinate $\lambda_2$ is obtained based on the above Expressions (3) to (5) established among: the provisional flow behavior index $n_a$; the second relative movement distance $\Delta L_2$, the second peak value $F_{T2}$ and the second convergent value $F_{Te2}$, at the second relative movement velocity $v_{p2}$; the plunger ratio $\kappa$; and the second dimensionless coordinate $\lambda_2$; or based on a graph or a table created based on the above Expressions (3) to (5).

Following thereto, a second dimensionless flow velocity $\Phi_2$ is obtained based on the above Expression (2) established among the provisional flow behavior index $n_a$, the obtained second dimensionless coordinate $\lambda_2$ and a second dimensionless flow velocity $\Phi_2$, or based on a graph or a table created based on the above Expression (2).

Then, a flow behavior index n of the sample 20 is obtained based on: the first dimensionless coordinate $\lambda_1$ and the first dimensionless flow velocity $\Phi_1$ at the first relative movement velocity $v_{p1}$; the second dimensionless coordinate $\lambda_2$ and the second dimensionless flow velocity $\Phi_2$ at the second relative movement velocity $v_{p2}$; and the above Expression (6).

When peak values and convergent values of a force at three or more relative movement velocities have been already obtained, for example, the above Expression (6) is referred to for each pair of two kinds of relative movement velocities $(v_{pi}, v_{pj})$, and values shown by an expression $(v_{pj}/\Phi_j)/(v_{pi}/\Phi_1)$" and values shown by an expression $(F_{cb\_j}/(L_0+L_{2\_j})\lambda_j^2)/(F_{cb\_i}/(L_0+L_{2\_i})\lambda_i^2)$" are respectively calculated. Then, in a logarithmic axis, the former values are plotted on the axis of ordinate and the latter values are plotted on the axis of abscissa. From an inclination of its approximate line, an inverse s (=1/n) of the flow behavior index n of the sample 20 is obtained.

Then, the obtained flow behavior index n is compared to the provisional flow behavior index $n_a$. When the obtained flow behavior index n is different from the provisional flow behavior index $n_a$, the method returns to the step of determining a provisional flow behavior index $n_a$. On the other hand, when the obtained flow behavior index n is equal to the provisional flow behavior index $n_a$, the method proceeds on to a succeeding step (H).

(H) When the first relative movement velocity $v_{p1}$ is represented as $v_p$, the first relative movement distance $\Delta L_1$ is represented as $\Delta L$, the first peak value $F_{T1}$ is represented as $F_T$, and the first convergent value $F_{Te1}$ is represented as $F_{Te}$, or when the second relative movement velocity $v_{p2}$ is represented as $v_p$, the second relative movement distance $\Delta L_2$ is represented as $\Delta L$, the second peak value $F_{T2}$ is represented as $F_T$, and the second convergent value $F_{Te2}$ is represented as $F_{Te}$, (or when the $m^{th}$ relative movement velocity $v_{pm}$ is represented as $v_p$, the $m^{th}$ relative movement distance $\Delta L_m$ is represented as $\Delta L$, the $m^{th}$ peak value $F_{Tm}$ is represented as $F_T$, and the $m^{th}$ convergent value $F_{Tem}$ is represented as $F_{Te}$,) the control unit 15 calculates an apparent viscosity $\mu_a$ of the sample 20 based on the $v_p$, the $\Delta L$, the $F_T$, the $F_{Te}$, the plunger ratio $\kappa$, the flow behavior index n, a density $\rho$ of the sample, a gravitational acceleration g, and the above Expression (1).

In the aforementioned step (G), when the convergent value $F_{Te}$ is judged to be equal to the buoyancy force $F_b$, the control unit 15 obtains an inverse s (=1/n) of the flow behavior index n of the sample 20 based on the first relative movement distance $\Delta L_1$ and the first peak value $F_{T1}$ at the first relative movement velocity $v_{p1}$, the second relative movement distance $\Delta L_2$ and the second peak value $F_{T2}$ at the second relative movement velocity $v_{p2}$, and the above Expression (8) (see step S104 in FIG. 5).

When peak values of a force at three or more relative movement velocities have been already obtained, the above Expression (8) is referred to for each pair of two kinds of relative movement velocities $(v_{pi}, v_{pj})$, and values shown by an expression $(v_{pj}/v_{pi})$" and values shown by an expression $(F_{cb2}/(L_0+L_{2\_j}))/(F_{cb1}/(L_0+L_{2\_i}))$" are respectively calculated. Then, in a logarithmic axis, the former values are plotted on the axis of ordinate and the latter values are plotted on the axis of abscissa. From an inclination of its approximate line, an inverse s (=1/n) of the flow behavior index n of the sample 20 is obtained.

Then, it is judged whether or not the obtained flow behavior index n is equal to 1 (see step S105 in FIG. 5). When the obtained flow behavior index n is judged to be equal to 1, the control unit 15 judges that the sample 20 belongs to a Newtonian fluid category, and applies thereto an analysis method for Newtonian fluid (see step S106 in FIG. 5). Namely, the control unit 15 calculates a viscosity of the sample 20 based on the viscosity measuring method described in the Patent Document 1 (JP2014-055928A). On the other hand, when the flow behavior index n is judged to be different from 1, the control unit 15 judges that the sample 20 belongs to a power-law fluid of non-Newtonian fluids, and applies thereto an analysis method for power-law fluid (see step S107 in FIG. 5). Namely, the control unit 15 calculates an apparent viscosity of the sample 20 based on the viscosity measuring method described in the Patent Document 2 (JP5596244B).

Next, concrete examples are explained.

As an apparatus including the driving unit 13, the measuring unit 14 and the control unit 15 of the viscosity measuring apparatus 10, there was used a rheometer CR-3000EX-S manufactured by Sun Scientific Co., Ltd. (sample stage velocity: 0.5 to 1200 mm/min, distance resolution: 0.01 mm, measurement load: ±20 N, load resolution: $10^{-4}$ N, maximum data fetch interval: 2000 points/sec). As the cylindrical container 11, there was used a stainless cup through which thermostatic water is circulated (internal diameter: 50.04 mm, depth: 66.60 mm). As the plunger 12, there was used a $\kappa$0.8 stainless plunger (external diameter: 40.00 mm, length: 61.6 mm, plunger ratio $\kappa$=0.8), a $\kappa$0.7 stainless plunger (external diameter: 34.98 mm, length: 61.6 mm, plunger ratio $\kappa$=0.7), a $\kappa$0.6 stainless plunger (external diameter: 30.01 mm, length: 61.6 mm, plunger ratio $\kappa$=0.6) or a $\kappa$0.5 stainless plunger (external diameter: 24.99 mm, length: 61.6 mm, plunger ratio $\kappa$=0.5).

A substance showing a standard viscosity of non-Newtonian fluid is not commercially available. Thus, as the sample 20 of non-Newtonian fluid, there were prepared a mayonnaise and a 4.5% solution of low methoxyl pectin (hereinafter LM pectin). The mayonnaise and the 4.5 solution of LM pectin belong to a Herschel-Bulkley fluid category of non-Newtonian fluids.

As the mayonnaise, a commercially available Kewpie mayonnaise (450 g) (manufactured by Kewpie Corporation, QPI, best before Aug. 3, 2015) bought in a store in a town was used. A density $\rho$ of the mayonnaise at 20° C., which was obtained by means of a Hubbard type pycnometer, was 942.3 kg/m³.

The 4.5% solution of LM pectin was a solution in which pectin LC810 (DuPont Nutrition & Health, Grindsted pectin LC 810), citric acid monohydrate (Wako Pure Chemical Industries, Ltd., special grade reagent), calcium citrate (Katayama Chemical Ltd., special grade reagent), calcium chloride (dihydrate) (Wako Pure Chemical Industries, Ltd., special grade reagent), sucrose (granulated sugar) (Mitsui Sugar Co., Ltd.), potassium sorbate (Taito Co., Ltd., food additive) and chrolamphenicol (Wako Pure Chemical Industries, Ltd., reagent) were blended with one another as shown in the Table 1 below.

TABLE 1

Composition of 4.5% Solution of LM Pectin

Ingredients (a) Buffer solution

| | |
|---|---|
| Citric Acid, monohydrate | 28.000 g |
| Tri-Calcium, di-citrate, tetra hydrate | 0.808 g |
| Demineralized water | 171.192 ml |
| Dissolved and fill up to 200 ml | |

(b) Calcium chloride solution

| | |
|---|---|
| Calcium chloride, dehydrate | 6.600 g |
| Demineralized water | 193.4 ml |
| Dissolved and fill up to 200 ml | |

(c) LM Pectin solution

| | |
|---|---|
| Demineralized water | 729.5 ml |
| Buffer solution | 30.00 ml |
| Calcium chloride solution | 10.00 ml |
| LM Pectin (Pectin LC 810) | 40.5 g |
| Sucrose | 90 g |
| Potassium sorbate | 0.90 g |
| Chrolamphenicol | 0.090 g |
| Final weight 900 g | |
| pH = 3.2 | |

To be specific, a buffer solution was made by mixing and dissolving by stirring 28.000 g of citric acid monohydrate and 0.808 g of calcium citrate in 171.192 ml of demineralized water, and by filling the solution into a sealed container up to a final weight of 200 ml. In addition, a calcium chloride solution was made by mixing and dissolving by stirring 6.600 g of calcium chloride (dihydrate) in 193.4 ml of demineralized water, and by filling the solution into a sealed container up to a final weight of 200 ml. 30.00 ml of the buffer solution and 10.00 ml of the calcium chloride solution were put into 729.5 ml of demineralized water. While they were heated and boiled, mixture of 90 g of sucrose (granulated sugar) and 40.5 g of LM pectin were put thereinto little by little, and they were dissolved by stirring. Further, 0.90 g of potassium sorbate and 0.090 g of chrolamphenicol were added thereto, dissolved and boiled. The solution was filled into a sealed container up to a final weight of 900 g, and thereafter cooled and left in a thermostatic chamber at 20° C. for 16 to 24 hours. A specific density of the 4.5% solution of LM pectin at 20° C., which was obtained by using a Hubbard pycnometer, was 1067.6 kg/m³.

A constitutive equation as a reference of the sample 20 of the non-Newtonian fluid was obtained from data measured by a cone-and-plate type viscometer.

To be specific, a strain control type rheometer ARES G2 (manufactured by TA Instrument, Co.) was used. By using a conical plunger having a diameter of 40 mm and a cone angle of 1 degree, a predetermined shear rate was given in a steady flow viscosity measuring mode. Measurement was carried out at 1000 points for one minute. A maximum value of a measured shear stress was obtained as a reference value. The reason for obtaining a maximum value of the shear stress is as follows. Namely, in the steady flow viscosity measurement by means of a cone-and-plate type viscometer, even when a measurement period of time is set at, for example, 30 seconds, measurement values largely disperse for respective measurement points. Thus, it is difficult to measure a viscosity in a stable steady flow condition. The possible reason for difficulty of measuring is as follows. A stress growth behavior is reported in polymer melt liquid and mayonnaise. Thus, it is estimated that a long relaxation time is required for polymer melt liquid and mayonnaise to reach a steady flow condition, therefore the measurement is carried out with a structure of a sample being destroyed. On the other hand, the translation type viscosity measurement according to this embodiment can carry out the measurement without a structure of a sample being destroyed. Thus, a stress-time curve obtained by the measurement of this embodiment can be considered to correspond to a maximum behavior value of the stress growth.

Figure 6:
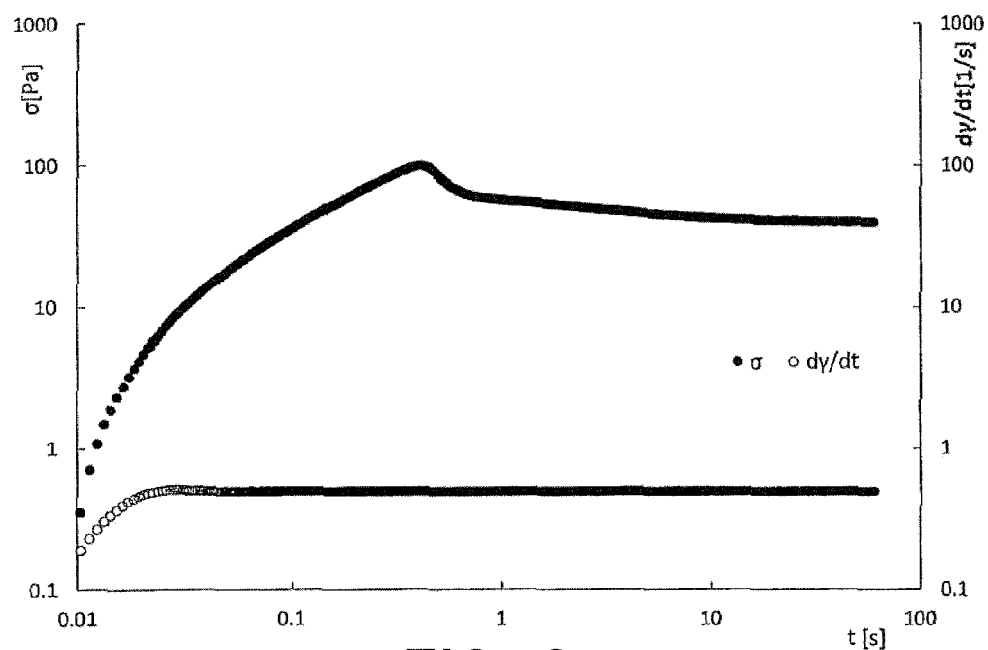
FIG. 6 is a graph showing a stress growth curve measured by means of a strain control type rheometer.
Figure 8:
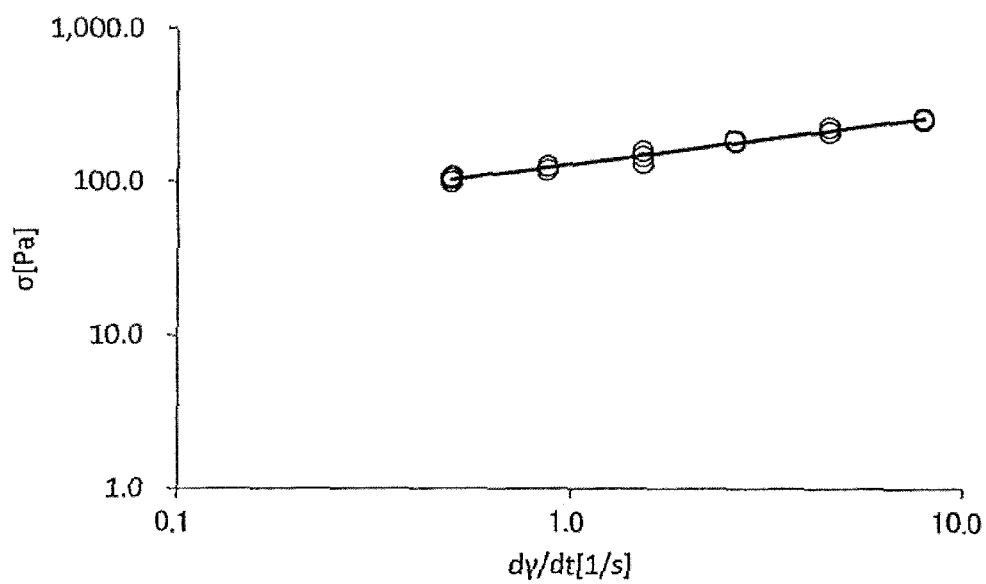
FIG. 8 is a graph showing a flow curve of mayonnaise measured by the strain control type rheometer based on a stress growth maximum value.
Figure 9:
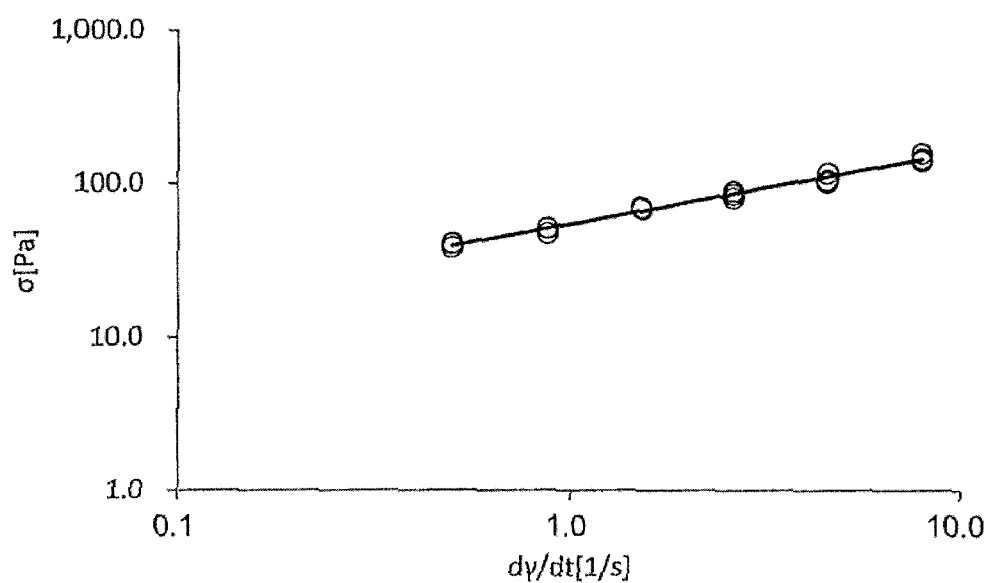
FIG. 9 is a graph showing a flow curve of LM pectin solution measured by the strain control type rheometer based on a stress growth maximum value.

FIG. 6 shows a stress growth behavior of the mayonnaise at 20° C., measured when a shear rate was 0.5 [1/s]. The shear rate $d\gamma/dt$ was set at any of the following six points not more than 10 [1/s], i.e., 0.5, 0.87, 1.52, 2.64, 4.59 and 8.01 [1/s] at which a stress growth phenomenon can be confirmed. The measurement operation was carried out three times for each shear rate. FIG. 8 shows a relationship between the shear rate $d\gamma/dt$ and a maximum value of a shear stress $\sigma$ of the mayonnaise, obtained by these measurement operations. FIG. 9 shows a relationship between a shear rate $d\gamma/dt$ and a maximum value of a shear stress $\sigma$ of the 4.5% solution of LM pectin. In FIGS. 8 and 9, the maximum values of the shear stress obtained by the measurement of stress growth does not largely disperse for the respective measurement points. Thus, it can be confirmed that the maximum value of the shear stress $\sigma$ shows a good correlationship within a range where the shear rate $d\gamma/dt=0.5$ to 8.01.

Figure 7:
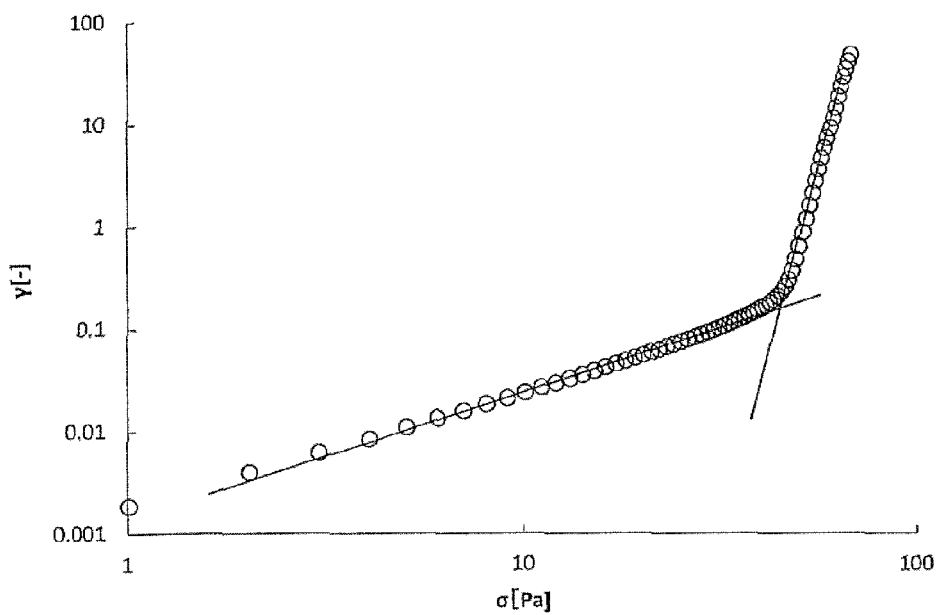
FIG. 7 is a graph showing a relationship between a stress and a strain measured by means of a stress control type rheometer.

Next, a stress control type rheometer Haake Rheo Stress 6000 (manufactured by Thermo Scientific Co.) was used. By using a conical plunger having a diameter of 40 mm and a cone angle of 1 degree, a predetermined shear rate was given to a sample such that a shear stress $\sigma$ ranges from 0 to 100 [Pa], and a strain $\gamma$ of the sample was measured. In a logarithmic axis, values of the shear stress $\sigma$ were plotted on the axis of abscissa, and values of the strain $\gamma$ were plotted on the axis of ordinate. A yield stress was obtained from a value of the axis of abscissa of an intersection point of their two approximate lines. FIG. 7 shows a relationship between the shear stress $\sigma$ and the strain $\gamma$ of the mayonnaise at 20° C. This measurement operation was carried out three times, and an average value of the three measurement operations was obtained.

Then, based on the yield value and the maximum value of the shear stress at each shear rate obtained by the above measurement, a constitutive equation as a reference of the sample was obtained. To be specific, the following Expression (9) was obtained as a constitutive equation of the mayonnaise, for example.

[NO 16]

$$\sigma = 39.070 + 90.002 \times \left(\frac{d\gamma}{dt}\right)^{0.4423} \qquad (9)$$

In addition, the following Expression (10) was obtained as a constitutive equation of the 4.5% solution of LM pectin.

[NO 17]

$$\sigma = 7.323 + 46.956 \times \left(\frac{d\gamma}{dt}\right)^{0.5231} \qquad (10)$$

Next, a measurement example according to this embodiment is described.

(A) The sample 20 was firstly put into the cylindrical container 11, and the plunger 12 was immersed into the sample 20 to an initial depth $L_0$=36.54 mm from a liquid level and stopped thereat. Afterward, by adjusting a temperature of the water circulated through the cylindrical container 11, an actual temperature of the sample 20 being measured was controlled to be 20±0.3° C.

(B) Then, under a condition in which a first relative movement distance $\Delta L_1$ of the plunger 12 was set at 9.61 mm in the driving unit 13, the plunger 12 was further immersed into the sample 20 at a first relative movement velocity $v_{p1}$=0.643 mm/s. Thereafter, the sample 20 was left for 5 minutes until the stress became convergent.

(C) During the further immersing operation and after the further immersing operation, a force applied to the plunger 12 from the sample 20 was measured. Based on the measurement result, a force-time curve was created so as to obtain a first peak value $F_{T1}$ and a first convergent value $F_{Te1}$ of the force applied to the plunger 12 from the sample 20. Note that, when the plunger 12 was moved at a high velocity, since a stopping distance was elongated by inertia, an actual first relative movement distance $\Delta L_1$ was calculated based on a time corresponding to the first peak value $F_{T1}$ shown by the force-time curve and the first relative movement velocity $v_{p1}$.

In the measurement example according to this embodiment, by sequentially (twice) repeating a step in which the plunger 12 was returned to the initial depth $L_0$=36.54 mm and stopped thereat, the step (B) and the step (C), the first peak value $F_{T1}$ and the first convergent value $F_{Te1}$ at the first relative movement velocity $v_{p1}$ of the plunger 12 were measured three times in total. When the plunger 12 was returned to the initial depth $L_0$=36.54 mm, as shown in FIG. 3(c), the sample adhered to the container 11 and the plunger 12, but an amount thereof was slight. Thus, the measurement operations were consecutively carried out, other than each measurement interval of two minutes that was provided between the measurement operations for waiting that the liquid level of the sample 20 was settled.

(D) Then, the plunger 12 was returned to the initial depth $L_0$=41.6 mm and stopped thereat.

(E) Thereafter, under a condition in which a second relative movement distance $\Delta L_2$ of the plunger 12 was set at 9.61 mm in the driving unit 13, the plunger 12 was further immersed into the sample 20 at a second relative movement velocity $v_{p2}$=1.058 mm/s. Then, the sample 20 was left for a predetermined period of time (5 minutes) until the stress became convergent.

(F) During the further immersing operation and after the further immersing operation, a force applied to the plunger 12 from the sample 20 was measured. Based on the measurement result, a force-time curve was created so as to obtain a second peak value $F_{T2}$ and a second convergent value $F_{Te2}$ of the force applied to the plunger 12 from the sample 20. An actual second relative movement distance $\Delta L_2$ was calculated also based on a time corresponding to the second peak value $F_{T2}$ shown by the force-time curve and the second relative movement velocity $v_{p2}$.

In the measurement example according to this embodiment, by sequentially (twice) repeating the step (D) to the step (F), the second peak value $F_{T2}$ and the second convergent value $F_{Te2}$ at the second relative movement velocity $v_{p2}$ of the plunger 12 were measured three times in total. Also, the measurement operations were consecutively carried out, other than each measurement interval of two minutes that was provided between the measurement operations for waiting that the liquid level of the sample 20 was settled.

In the measurement example according to this embodiment, the step (D), the step (E) in which the relative movement velocity of the plunger 12 was changed to one of a third relative movement velocity $v_{p3}$=1.740 mm/s, a fourth relative movement velocity $v_{p4}$=2.860 mm/s, a fifth relative movement velocity $v_{p5}$=4.700 mm/s and a sixth relative movement velocity $v_{p6}$=7.727 mm/s, and the step (F) were repeated with measurement intervals of two minutes therebetween.

Namely, the plunger 12 was returned to the initial depth $L_0$=36.54 mm and stopped thereat. Under a condition in which a third relative movement distance $\Delta L_3$ of the plunger 12 was set at 9.61 mm in the driving unit 13, the plunger 12 was further immersed into the sample 20 at the third relative movement velocity $v_{p3}$=1.740 mm/s. During the further immersing operation and after the further immersing operation, a force applied to the plunger 12 from the sample 20 was measured. Based on the measurement result, a force-time curve was created so as to obtain a third peak value $F_{T3}$ and a third convergent value $F_{Te3}$ of the force applied to the plunger 12 from the sample 20. An actual third relative movement distance $\Delta L_3$ was calculated also based on a time corresponding to the third peak value $F_{T3}$ shown by the force-time curve and the third relative movement velocity $v_{p3}$. By repeating the above steps, the third peak value $F_{T3}$ and the third convergent value $F_{Te3}$ at the third relative movement velocity $v_{p3}$ of the plunger 12 were measured three times in total.

Then, the plunger 12 was returned to the initial depth $L_0$=36.54 mm and stopped thereat. Under a condition in which a fourth relative movement distance $\Delta L_4$ of the plunger 12 was set at 9.61 mm in the driving unit 13, the plunger 12 was further immersed into the sample 20 at the fourth relative movement velocity $v_{p4}$=2.860 mm/s. During the further immersing operation and after the further immersing operation, a force applied to the plunger 12 from the sample 20 was measured. Based on the measurement result, a force-time curve was created so as to obtain a fourth peak value $F_{T4}$ and a fourth convergent value $F_{Te4}$ of the force applied to the plunger 12 from the sample 20. An actual fourth relative movement distance $\Delta L_4$ was calculated also based on a time corresponding to the fourth peak value $F_{T4}$ shown by the force-time curve and the fourth relative movement velocity $v_{p4}$. By repeating the above steps, the fourth peak value $F_{T4}$ and the fourth convergent value $F_{Te4}$ at the fourth relative movement velocity $v_{p4}$ of the plunger 12 were measured three times in total.

Then, the plunger 12 was returned to the initial depth $L_0$=36.54 mm and stopped thereat. Under a condition in which a fifth relative movement distance $\Delta L_5$ of the plunger 12 was set at 9.61 mm in the driving unit 13, the plunger 12 was further immersed into the sample 20 at the fifth relative movement velocity $v_{p5}$=4.700 mm/s. During the further immersing operation and after the further immersing operation, a force applied to the plunger 12 from the sample 20 was measured. Based on the measurement result, a force-time curve was created so as to obtain a fifth peak value $F_{T5}$ and a fifth convergent value $F_{Te5}$ of the force applied to the plunger 12 from the sample 20. An actual fifth relative movement distance $\Delta L_5$ was calculated also based on a time corresponding to the fifth peak value $F_{T5}$ shown by the force-time curve and the fifth relative movement velocity $v_{p5}$. By repeating the above steps, the fifth peak value $F_{T5}$ and the fifth convergent value $F_{Te5}$ corresponding to the fifth relative movement velocity $v_{p5}$ of the plunger 12 were measured three times in total.

Then, the plunger 12 was returned to the initial depth $L_0$=36.54 mm and stopped thereat. Under a condition in which a sixth relative movement distance $\Delta L_6$ of the plunger 12 was set at 9.61 mm in the driving unit 13, the plunger 12 was further immersed into the sample 20 at the sixth relative movement velocity $v_{p6}$=7.727 mm/s. During the further immersing operation and after the further immersing operation, a force applied to the plunger 12 from the sample 20 was measured. Based on the measurement result, a force-time curve was created so as to obtain a sixth peak value $F_{T6}$ and a sixth convergent value $F_{Te6}$ of the force applied to the plunger 12 from the sample 20. An actual sixth relative movement distance $\Delta L_6$ was calculated also based on a time corresponding to the sixth peak value $F_{T6}$ shown by the force-time curve and the sixth relative movement velocity $v_{p6}$. By repeating the above steps, the sixth peak value $F_{T6}$ and the sixth convergent value $F_{Te6}$ at the sixth relative movement velocity $v_{p6}$ of the plunger 12 were measured three times in total.

By the above steps, the peak values $F_{T1}$ to $F_{T6}$ of the forces corresponding to the six kinds of relative movement velocities $v_{p1}$ to $v_{p6}$ were obtained respectively three times. The following Table 2 shows average values of the peak values $F_T$ and $F_{Te}$ of the forces corresponding to the respective relative movement velocities $v_{p1}$ to $v_{p6}$, which were obtained when a mayonnaise was used as the sample 20 and the κ0.6 stainless plunger was used as the plunger 12, for example.

TABLE 2

Measurement Result of Mayonnaise in Measurement Example (k = 0.6) of Embodimenr (average value measured three times at each $v_p$)

| $v_p$[m/s] × $10^{-3}$ | 0.643 | 1.058 | 1.740 | 2.860 | 4.700 | 7.727 |
|---|---|---|---|---|---|---|
| $F_T$[N] | 1.407 | 1.543 | 1.788 | 1.933 | 2.157 | 2.498 |
| $F_{Te}$[N] | 0.298 | 0.298 | 0.298 | 0.298 | 0.298 | 0.298 |
| $n_a$ | 0.3725 | 0.3725 | 0.3725 | 0.3725 | 0.3725 | 0.3725 |
| λ | 0.78174 | 0.78210 | 0.78224 | 0.78281 | 0.78309 | 0.78331 |
| Φ | 0.00045 | 0.00055 | 0.00067 | 0.00079 | 0.00091 | 0.00106 |

(G) Then, after the fact that the convergent values $F_{Te1}$ to $F_{Te6}$ of the forces applied to the plunger 12 from the sample 20 at the relative movement velocities $v_{p1}$ to $v_{p6}$ were larger than the buoyancy force $F_b$ applied to the plunger 12 from the sample 20 was confirmed, based on the above Expressions (2) to (5) and the following Expression (6) established among: the respective relative movement distances $\Delta L_1$ to $\Delta L_6$, the respective peak values $F_{T1}$ to $F_{T6}$ and the respective convergent values $F_{Te1}$ to $F_{Te6}$, at the respective relative movement velocities $v_{p1}$ to $v_{p6}$; a plunger ratio κ=$R_i/R_O$; and a flow behavior index n of the sample 20; the flow behavior index n of the sample 20 was obtained.

To be specific, a provisional flow behavior index $n_a$ was firstly set at 0.3725, for example.

Then, a first dimensionless coordinate $\lambda_1$, which satisfies the above Expressions (3) to (5) established among: the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio κ; and the first dimensionless coordinate $\lambda_1$; was obtained by calculation using a numerical analysis program (manufactured by Fujitsu Limited) capable of doing an approximate calculation by the Simpson method. Then, based on the first dimensionless coordinate $\lambda_1$, the provisional flow behavior index $n_a$ and the above Expression (2), a first dimensionless flow velocity $\Phi_1$ was obtained by calculation.

Similarly, second dimensionless coordinates $\lambda_2$ to $\lambda_6$, which satisfy the above Expressions (3) to (5) established among: the provisional flow behavior index $n_a$; the respective relative movement distances $\Delta L_2$ to $\Delta L_6$, the relative peak values $F_{T2}$ to $F_{T6}$, and the respective convergent values $F_{Te2}$ to $F_{Te6}$, at the respective relative movement velocities $v_{p2}$ to $v_{p6}$; the plunger ratio κ; and the dimensionless coordinates $\lambda_2$ to $\lambda_6$, were obtained by calculation using the above numerical analysis program (manufactured by Fujitsu Limited). Then, based on the dimensionless coordinates $\lambda_2$ to $\lambda_6$ at the respective movement velocities $v_{p2}$ to $v_{p6}$, the provisional flow behavior index $n_a$ and the above Expression (2), dimensionless flow velocities $\Phi_2$ to $\Phi_6$ were obtained by calculation.

The above Table (2) shows the provisional flow behavior indexes $n_a$, the dimensionless coordinates λ and the dimensionless flow velocities Φ obtained at the respective relative movement velocities $v_{p2}$ to $v_{p6}$.

Figure 10:
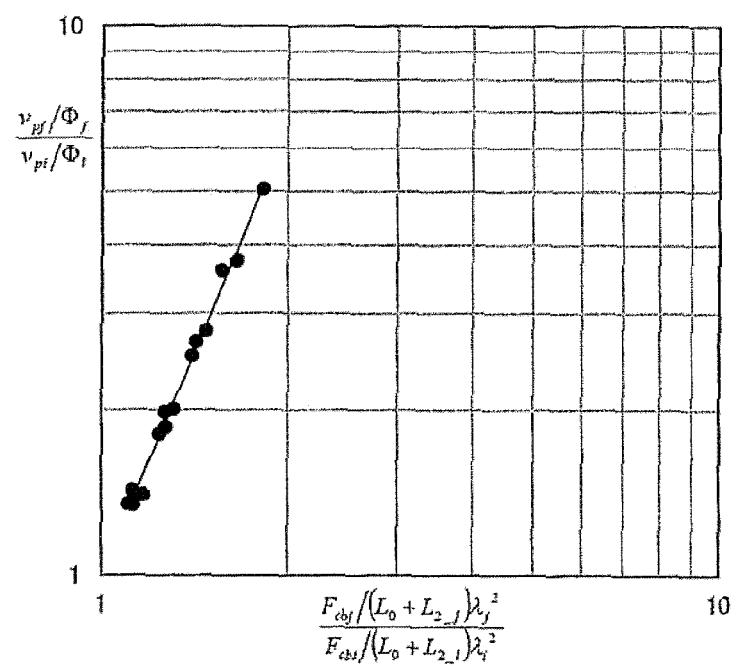
FIG. 10 is a graph created for obtaining a flow behavior index n of a sample, in a measurement example according to one embodiment of the present invention.

Then, based on the dimensionless coordinates $\lambda_1$ to $\lambda_6$ and the dimensionless flow velocities $\Phi_2$ to $\Phi_6$ at the respective relative movement velocities $v_{p2}$ to $v_{p6}$, and the above Expression (6), the flow behavior index n of the sample 20 was obtained. To be specific, the above Expression (6) is referred to for each pair of relative movement velocities ($v_{pi}$, $v_{pj}$), and values shown by an expression $(v_{pj}/\Phi_j)/(v_{pi}/\Phi_i)"$ and values shown by an expression $(F_{cb\_i}/(L_0+L_{2\_j})\lambda_j^2/(F_{cb\_i}/(L_0+L_{2\_i})\lambda_i^2)"$ were respectively calculated. Then, as shown in FIG. 10, in a logarithmic axis, the former values were plotted on the axis of ordinate and the latter values were plotted on the axis of abscissa. From an inclination of its approximate line, an inverses (=1/n) of the flow behavior index n of the sample 20 was obtained. Herein, based on FIG. 10, s=2.6877 (n=0.3721) was obtained.

The obtained flow behavior index n was compared to the provisional flow behavior index $n_a$. When the obtained flow behavior index n was different from the provisional flow behavior index $n_a$, the calculation for obtaining the flow behavior index n was repeated until the obtained flow behavior index n became equal to the provisional behavior index $n_a$.

(H) Then, based on: the relative movement velocity vp, the relative movement distance ΔL, the force peak value $F_{T1}$, the force convergent value $F_{Te1}$, at each six kinds of relative movement velocities $v_{p1}$ to $v_{p6}$; the plunger ratio κ; the flow behavior index n; a density ρ of the sample 20; a gravitational acceleration g; and the above Expression (1); a shear rate dγ/dt of the sample 20, a shear stress $\sigma_w$ thereof and an apparent viscosity $\mu_a$ thereof were respectively calculated.

Figure 11:
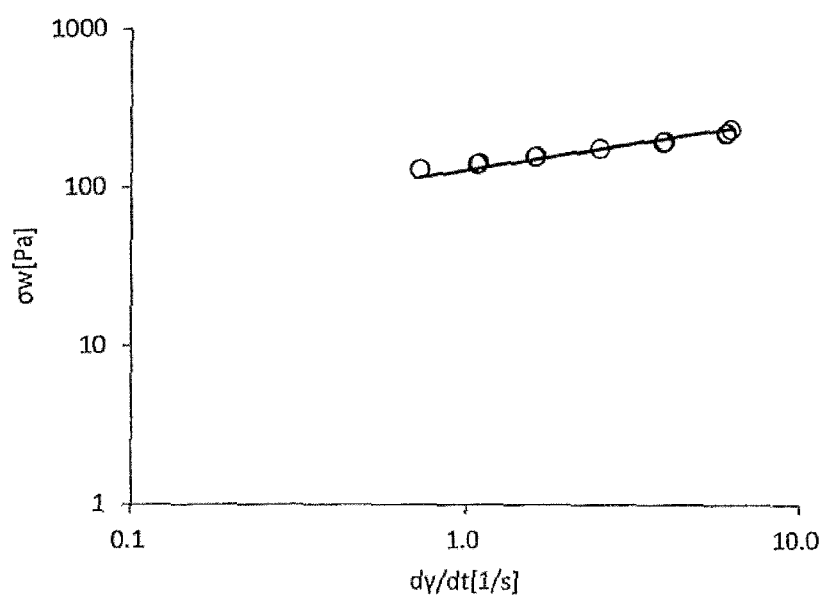
FIG. 11 is a graph showing a measurement result when mayonnaise was used as a sample, in a measurement example according to one embodiment of the present invention.

FIG. 11 shows a measurement result in which, for example, a mayonnaise was used as the sample 20 and a κ0.6 stainless plunger was used as the plunger 12. In FIG. 11, a circle symbol (○) shows an actual measurement value in the measurement example according to this embodiment, and a solid line shows a flow curve (reference line) of the mayonnaise measured by a cone-and-plate type viscometer based on a stress growth maximum value shown in the above Expression (9).

In order to evaluate each measurement example according to this embodiment, there was calculated a root mean square error (hereinafter RMSE) shown by the following Expression (11) in which the actual measurement value $\sigma_w$ of the shear stress at each shear rate dγ/dt was represented as $\sigma_{wi}$, and a value on the reference line at the shear rate dγ/dt was represented as $\sigma_{w0}$.

[NO 18]

$$RMSE = \sqrt{\frac{1}{n}\sum_{i=1}^{n}\frac{(\sigma_{wi}-\sigma_{w0})^2}{\sigma_{w0}^2}} \quad (11)$$

The following Table 3 shows the RMSE of each sample 20 of non-Newtonian fluid for each plunger ratio κ.

TABLE 3

Analysis Result of Measurement Example of Embodiment:

| | RMSE | |
|---|---|---|
| Section | Mayonnaise | LM Pectin Solution |
| κ = 0.8 | 0.237 | 0.199 |
| κ = 0.7 | 0.092 | 0.053 |
| κ = 0.6 | 0.065 | 0.093 |
| κ = 0.5 | 0.040 | 0.022 |

Next, a comparative measurement example by the back extrusion (BE) method is explained.

Figure 12:
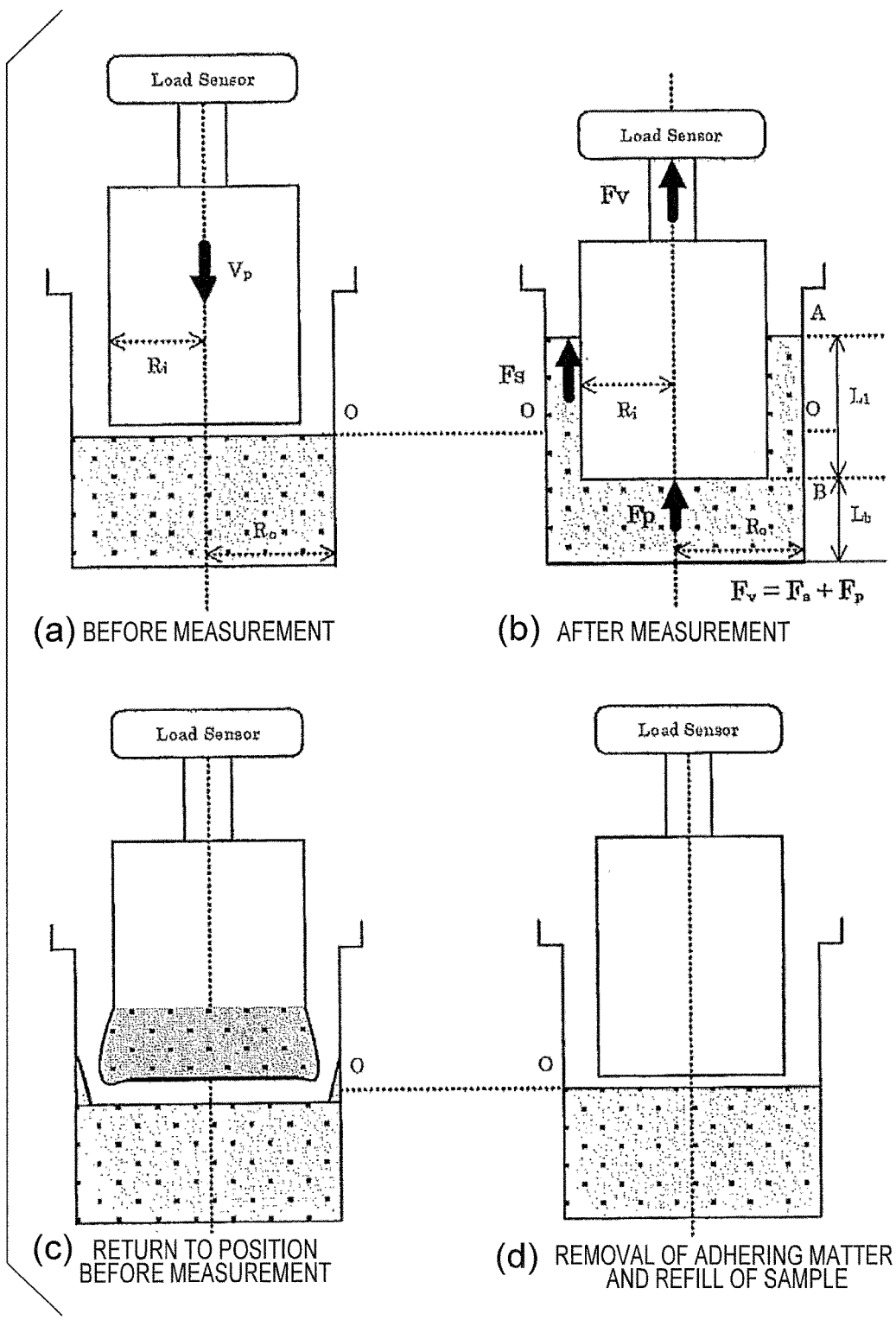
FIG. 12 is a view for explaining an operation of the viscosity measuring apparatus in the BE method.

(a) The sample 20 was firstly put into the cylindrical container 11, and the plunger 12 was positioned at an initial position above a liquid level (see FIG. 12(a)). Afterward, by adjusting a temperature of the water circulated through the cylindrical container 11, an actual temperature of the sample 20 being measured was controlled to be 20±0.3° C.

(b) Then, under a condition in which a relative movement distance ΔL of the plunger 12 was set at 33.00 mm, the plunger 12 was immersed into the sample 20 at a relative movement velocity $v_p$=0.643 mm. Thereafter, the plunger 12 was left for 5 minutes until a stress became convergent (see FIG. 12(b)).

(c) During the immersing operation and after the immersing operation, a force applied to the plunger 12 from the sample 20 was measured. A force-time curve was created based on the measurement result, and a peak value $F_T$ and a convergent value $F_{Te}$ of the force applied to the plunger 12 from the sample 20 were obtained. When the plunger 12 was moved at a high speed, a stop distance elongated because of inertia. Thus, based on a time corresponding to the peak value $F_T$ shown by the force-time curve and the relative movement velocity $v_p$, an actual relative movement distance ΔL was calculated.

(d) Then, the plunger was drawn up from the liquid level, and was located at the initial position. At this time, as shown in FIG. 12(c), since the sample 20 adhered to a wall surface of the container 11 and a wall surface of the plunger 12, the adhering sample 20 was carefully removed from the container 11 and the plunger 12, and a new sample 20 was added to the container 11 such that the liquid level returned to the original height (see FIG. 12(d)).

After that, in this comparative measurement example, by repeating the step (b), the step (c) and the step (d) sequentially (twice), the peak value $F_T$ and the convergent value $F_{Te}$ of the forces of the sample 20 at the first relative movement velocity $v_{p1}$ of the plunger 12 were measured respectively three times.

(e) By sequentially repeating the step (b) in which the relative movement velocity of the plunger 12 was change to the step (d), the peak value $F_T$ and the convergent value $F_{Te}$ of the force corresponding to the six kinds of relative movement velocities were obtained respectively three times. The following Table 4 shows average values of the peak forces $F_T$ and the convergent value $F_{Te}$ of the force of the sample 20 at the relative movement velocities $v_{p1}$ to $v_{p8}$ in total, when a mayonnaise was used as the sample 20 and the κ0.6 stainless plunger was used as the plunger 12, for example.

TABLE 4

Measurement Result of Mayonnaise in Measurement Comparative Example (κ = 0.6) (average value measured three times at each $v_p$):

| $v_p$[m/s] × 10⁻³ | 0.643 | 1.058 | 1.740 | 2.860 | 4.700 | 7.727 |
|---|---|---|---|---|---|---|
| $F_T$[N] | 1.481 | 1.569 | 1.741 | 1.858 | 1.956 | 2.159 |
| $F_{Te}$[N] | 0.516 | 0.477 | 0.464 | 0.452 | 0.432 | 0.420 |
| $n_a$ | 0.25785 | 0.25785 | 0.25785 | 0.25785 | 0.25785 | 0.25785 |
| λ | 0.78100 | 0.78115 | 0.78134 | 0.78151 | 0.78160 | 0.78176 |
| Φ | 0.00015 | 0.00016 | 0.00019 | 0.00022 | 0.00024 | 0.00027 |

Next, according to the analysis method of Herschel-Bulkley fluid by the BE method, which is described in the above Non-Patent document 3, a shear rate dγ/dt and a shear stress $\sigma_w$ of the sample 20 were respectively calculated at each of the six kinds of relative movement velocities $v_{p1}$ to $v_{p6}$.

Figure 13:
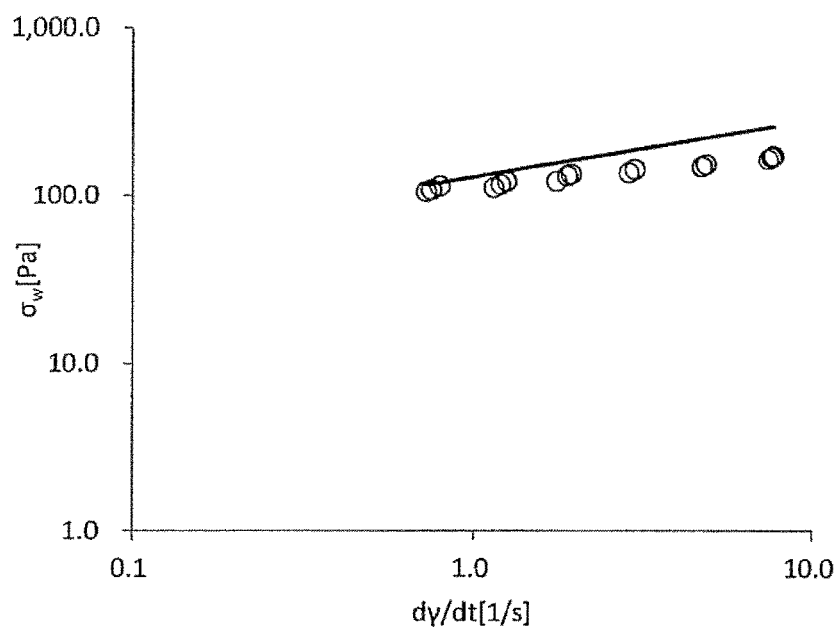
FIG. 13 is a graph showing a measurement result when mayonnaise was used as a sample, in a comparative measurement example by the BE method.

FIG. 13 shows a measurement result in which, for example, a mayonnaise was used as the sample 20 and a κ0.6 stainless plunger was used as the plunger 12. In FIG. 13, a circle symbol (○) shows an actual measurement value in the comparative measurement example, and a solid line shows a flow curve (reference line) of the mayonnaise measured by a cone-and-plate type viscometer based on a stress growth maximum value shown in the above Expression (9).

In order to evaluate each comparative measurement example, there was calculated the RMSE shown in the above Expression (11) based on the actual measurement value $\sigma_{wi}$ of the shear stress at each shear rate dγ/dt and value $\sigma_{w0}$ on the reference line at the shear rate dγ/dt. The following Table 5 shows the RMSE of each sample 20 of non-Newtonian fluid for each plunger ratio κ.

TABLE 5

Analysis Result of Measurement Comparative Example:

| | RMSE | |
|---|---|---|
| Section | Mayonnaise | LM Pectin Solution |
| κ = 0.8 | 0.443 | 0.272 |
| κ = 0.7 | 0.305 | 0.198 |
| κ = 0.6 | 0.240 | 0.105 |
| κ = 0.5 | 0.117 | 0.126 |

The present inventors actually verified that, in the comparative measurement example, the RMSE was large at any of the plunger ratio κ, i.e., the flow behavior properties of the Herschel-Bulkley fluid could not be exactly measured. On the other hand, in the measurement example according to this embodiment, whenever any of the four kinds of plunger ratios (K=0.8, 0.7, 0.6, 0.5) was selected, an error was smaller than the comparative measurement example, i.e., the flow behavior properties of the Herschel-Bulkley fluid could be exactly measured. In particular, when the plunger ratio κ was in the rang between 0.5 and 0.7, the flow behavior properties of the Herschel-Bulkley fluid could be measured with significantly good precision of not more than 0.1 of RMSE.

Namely, according to the above embodiment, as compared with the back extrusion (BE) method, a measurement precision of an apparent viscosity of the Herschel-Bulkley fluid can be significantly improved.

Preferably, the first, second relative movement distances $\Delta L_1$, $\Delta L_2$ (and the $m^{th}$ relative movement distance $\Delta L_m$) are smaller than the initial depth $L_0$. According to this embodiment, since the deformation of the sample 20 is small, the measurement can be repeated plural times without removing the sample 20 adhering to the container 11 and the plunger 12. Thus, as compared with the BE method, the measurement time can be notably reduced.

In this embodiment, in the step (B) and the step (E), the plunger 12 is further immersed by the first and second relative movement distances $\Delta L_1$ and $\Delta L_2$ which are different from each other. However, not limited thereto, in the step (B) and the step (E), the plunger 12 may be further immersed at the same relative movement distances $\Delta L$.

In addition, in this embodiment, an apparent viscosity $\mu_a$ of the sample 20 is obtained based on the first peak value $F_{T1}$ and the first convergent value $F_{Te1}$ or the second peak value $F_{T2}$ and the second convergent value $F_{Te2}$, which are used in the calculation of the flow behavior index n of the sample 20. However, not limited thereto, an apparent viscosity $\mu_a$ of the sample 20 may be obtained based on a seventh peak value $F_{T7}$ and a seventh convergent value $F_{Te7}$ (corresponding to the third peak value $F_{T3}$ and the third convergent value $F_{Te3}$ in claims 7, 14 and 21), which are not used in the calculation of the flow behavior index n of the sample 20. Namely, after the step (G), there may be performed: a step (H) in which the plunger 12 is returned coaxially with the cylindrical container 11 to the initial depth $L_0$ and stopped thereat; a step (I) in which the plunger 12 is further immersed into the sample 20 coaxially with the cylindrical container 11 at a seventh relative movement velocity $v_{p7}$ by a seventh relative movement distance $\Delta L_7$, and during the further immersing operation and after the further immersing operation, a force applied to the plunger 12 from the sample 20 is measured with a passage of time; a step (J) in which a seventh peak value $F_{T7}$ and a seventh convergent value $F_{Te7}$ of the force applied to the plunger 12 from the sample 20 are obtained, based on measured values of the force caused by the relative movement of the plunger 12 at the seventh relative movement velocity $v_{p7}$; and a step (K) in which, when the seventh relative movement velocity $v_{p7}$ is represented as $v_p$, the seventh relative movement distance $\Delta L_7$ is represented as $\Delta L$, the seventh peak value $F_{T7}$ is represented as $F_T$ and the seventh convergent value $F_{Te7}$ is represented as $F_{Te}$, an apparent viscosity $\mu_a$ of the sample 20 is calculated based on the $v_p$, the $\Delta L$, the $F_T$ and the $F_{Te}$, the plunger ratio $\kappa$, the flow behavior index n, a density $\rho$ of the sample 20, a gravitational acceleration g, and the above Expression (1).

As described above, the control unit 15 may be formed of a computer system, but the present invention also covers a program executed by a computer system for realizing the control unit 15 and a computer-readable storage medium storing the program.

Further, when the control unit 15 is realized by a program such as OS (second program) executed on the computer system, the present invention also covers a program including various commands for controlling the program such as OS, and a storage medium storing the program.

Herein, the storage medium includes not only a flexible disc that can be recognized as itself, but also a network transmitting various signals.

Finally, a measuring theory of the viscosity measuring method according to the embodiment of the present invention is described.

Firstly, as an analysis condition, a ratio of the external radius $R_i$ of the plunger with respect to the internal radius $R_0$ of the cylindrical container is represented by the following Expression (12) as a plunger ratio $\kappa$.

[NO 19]

$$\kappa = \frac{R_i}{R_0} \quad (12)$$

When a force (stress) $F_{cb}$ applied to the plunger is initialized to zero at a position where the plunger is immersed into the sample by the initial depth $L_0$ and stopped thereat, the force $F_{cb}$ can be obtained by deducting a buoyancy force of the plunger at a liquid depth $L_2$ from the peak value $F_T$, which is a maximum stress after the stationary fluidity is obtained during the further immersing operation and after the further immersing operation, and is represented by the following Expression (13).

$$F_{cb} = F_T - F_b \quad (13)$$

In a case of a fluid not having a yield stress $F_y$, a stress $F_{Te}$ that becomes convergent after the sample is left for a predetermined period of time is represented by the following Expression (14), because it is equivalent to the buoyancy force $F_b$ applied to the plunger 12 from the sample 20. On the other hand, in a case of a fluid having a yield stress $F_y$, a stress $F_{Te}$ is represented by the following Expression (15).

$$F_{Te} = F_b \quad (14)$$

[NO 22]

$$F_{Te} = F_b + F_y \quad (15)$$

Herein, the buoyancy force $F_b$ is represented by the following Expression (16).

[NO 23]

$$F_b = \pi R_i^2 L_2 \rho g \quad (16)$$

In addition, a yield stress $\sigma_y$ is represented by the following Expression (17).

[NO 24]

$$\sigma_y = \frac{F_y}{2\pi R_i (L_0 + L_2)} \quad (17)$$

In addition, a dimensionless yield stress $T_0$ is represented by the following Expression (18).

[NO 25]

$$T_0 = \frac{F_y}{F_{cb}} \quad (18)$$

Figure 14:
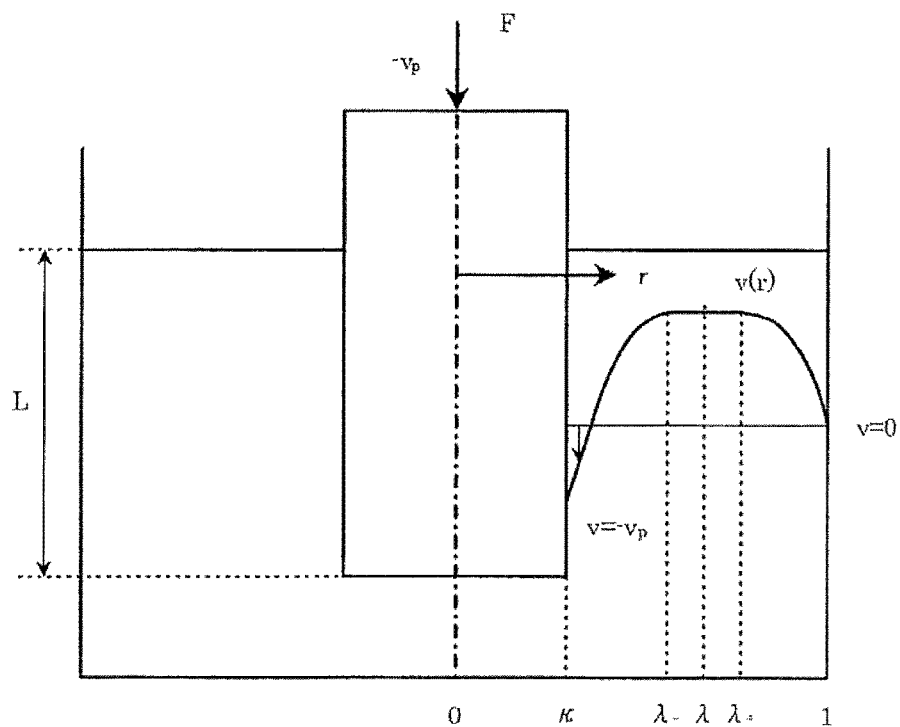
FIG. 14 is a view used for explaining a measurement theory of a viscosity measuring method according to one embodiment of the present invention.

In a radiation coordinate system shown in FIG. 14, when a center of a plug flow part is represented as $\lambda$, a boundary closer to a central axis is represented as $\lambda_-$ and a boundary farther therefrom is represented as $\lambda_+$, the relationships of the following Expressions (19) to (21) are established. Thus, by using the dimensionless yield stress $T_0$ and the dimensionless coordinate $\lambda$, the relationships of the above Expressions (4) and (5) can be obtained.

[NO 26]
$$\lambda_- = \lambda_+ - T_0 \qquad (19)$$

[NO 27]
$$\lambda^2 = \lambda_+(\lambda_+ - T_0) \qquad (20)$$

[NO 28]
$$\lambda^2 = \lambda_- \lambda_+ \qquad (21)$$

In this area, when an inverse S of the flow behavior index n is supposed, the above Expression (3) is established about the dimensionless coordinate $\lambda$. The dimensionless flow velocity $\Phi$ is represented by the above Expression (2) by suing the dimensionless coordinate $\lambda$.

In the dimensionless flow velocity $\Phi$ obtained from the measurement data at different relative movement velocities of the plunger, the relationship of the following Expression (22) is established. Thus, by deforming the expression like the above Expression (6), an inverse s of the flow behavior index n can be obtained.

[NO 29]
$$\frac{\Phi_1}{\Phi_2} = \left(\frac{\frac{F_{cb2}}{L_2 \lambda_2^2}}{\frac{F_{cb1}}{L_1 \lambda_1^2}}\right)^s \left(\frac{v_{p1}}{v_{p2}}\right) \qquad (22)$$

By repeating the calculation such that the thus obtained flow behavior index n and the supposed flow behavior index become equal, an exact flow behavior index n, an exact dimensionless coordinate $\lambda$ and an exact dimensionless flow velocity $\Phi$ can be obtained.

A dimensionless shear stress $T_w$ is expressed by the following Expression (23) by using the dimensionless coordinate $\lambda$.

[NO 30]
$$T_w = \frac{\lambda^2}{\kappa} - \kappa \qquad (23)$$

A pressure drop P is represented by the following Expression (24).

[NO 31]
$$P = \frac{2\sigma_y}{T_0 R_0} \qquad (24)$$

A consistency coefficient K is represented by the following Expression (25).

[NO 32]
$$K = \frac{PR_0}{2}\left(\frac{\Phi R_0}{v_p \kappa^2}\right)^n \qquad (25)$$

A shear rate $d\gamma/dt$ is represented by the following Expression (26).

[NO 33]
$$\frac{d\gamma}{dt} = \left(\frac{\lambda^2}{\kappa} - \kappa - T_0\right)^s \left(\frac{PR_0}{2K}\right)^s \qquad (26)$$

A shear stress $\sigma$ is represented by the following Expression (27).

[NO 34]
$$\sigma_w = \frac{T_w P R_0}{2} \qquad (27)$$

Therefore, from these expressions, an apparent viscosity $\mu_a$ of the sample is represented by the above Expression (1).
10 Viscosity measuring apparatus
11 Cylindrical container
12 Plunger
13 Driving unit
13a Base seat
13b Support member
14 Measuring unit
15 Control unit
16 Housing
17 Plunger attachment
18 Slit
20 Sample

The invention claimed is:
1. A method of measuring an apparent viscosity of a sample of non-Newtonian fluid comprising:
(A) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;
(B) a step in which the plunger is further immersed into the sample coaxially with the cylindrical container at a first relative movement velocity $v_{p1}$ by a first relative movement distance $\Delta L_1$, and during the further immersing operation and after the further immersing operation, a force applied to the plunger from the sample is measured with a passage of time;
(C) a step in which a first peak value $F_{T1}$ and a first convergent value $F_{Te1}$ of the force applied to the plunger from the sample are obtained, based on measured values of the force caused by the relative movement of the plunger at the first relative movement velocity $v_{p1}$;
(D) a step in which the plunger is returned coaxially with the cylindrical container to the initial depth $L_0$ and stopped thereat;
(E) a step in which the plunger is further immersed into the sample coaxially with the cylindrical container at a second relative movement velocity $v_{p2}$ by a second relative movement distance $\Delta L_2$, and during the further immersing operation and after the further immersing operation, a force applied to the plunger from the sample is measured with a passage of time;

(F) a step in which a second peak value $F_{T2}$ and a second convergent value $F_{Te2}$ of the force applied to the plunger from the sample are obtained, based on measured values of the force caused by the relative movement of the plunger at the second relative movement velocity $v_{p2}$;

(G) a step in which, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n is obtained; and (H) a step in which, when the first relative movement velocity $v_{p1}$ is represented as $v_p$, the first relative movement distance $\Delta L_1$ is represented as $\Delta L$, the first peak value $F_{T1}$ is represented as $F_T$, and the first convergent value $F_{Te1}$ is represented as $F_{Te}$, or when the second relative movement velocity $v_{p2}$ is represented as $v_p$, the second relative movement distance $\Delta L_2$ is represented as $\Delta L$, the second peak value $F_{T2}$ is represented as $F_T$, and the second convergent value $F_{Te2}$ is represented as $F_{Te}$, an apparent viscosity $\mu_a$ of the sample is calculated based on the $v_p$, the $\Delta L$, the $F_T$, the $F_{Te}$, the plunger ratio $\kappa$, the flow behavior index n, a density $\rho$ of the sample, a gravitational acceleration g, and the following Expression (1):

[NO 1]

$$\mu_a = \frac{\sigma_w}{dy/dt} = \frac{\sigma_0 + K\left(\frac{dy}{dt}\right)^n}{dy/dt} \quad (1)$$

in which $$\sigma_w = \frac{T_w P R_0}{2}, \quad \frac{dy}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, \quad P = \frac{2\sigma_y}{T_0 R_0}, \quad T_w = \frac{\lambda^2}{\kappa} - \kappa,$$

$$\Phi = \left\{\int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx\right\} \kappa^2 - \quad (2)$$

$$\int_\kappa^{\lambda_-} (\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx, \quad (3)$$

$$s = \frac{1}{n},$$

$$\lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \quad \sigma_y = \frac{F_y}{2\pi R_i(L_0 + L_2)}, \quad F_y = F_{Te} - F_b,$$

$$F_{cb} = F_T - F_b, \quad F_b = \pi R_i^2 L_2 \rho g, \quad L_2 = \frac{\Delta L}{1 - \kappa^2}.$$

2. The viscosity measuring method according to claim 1, wherein the first relative movement distance $\Delta L_1$ and the second relative movement distance $\Delta L_2$ are smaller than the initial depth $L_0$.

3. The viscosity measuring method according to claim 1, wherein in the step of obtaining the flow behavior index n, it is judged whether the convergent value $F_{Te}$ of the force applied to the plunger from the sample at the first relative movement velocity $v_{p1}$ or the second relative movement velocity $v_{p2}$ is larger or not than a buoyancy force $F_b$ applied to the plunger from the sample, and when the convergent value $F_{Te}$ is judged to be larger than the buoyancy force $F_b$, the process for obtaining the flow behavior index n is performed.

4. The viscosity measuring method according to claim 1, wherein the relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; the plunger ratio $\kappa$; and the flow behavior index n of the sample includes the above Expressions (2) to (5) and the following Expression (6):

[NO 2]

$$s = \frac{1}{n} = \frac{\ln\left(\frac{v_{p2}/\Phi_2}{v_{p1}/\Phi_1}\right)}{\ln\left(\frac{F_{cb2}/(L_0 + L_{2\_2})\lambda_2^2}{F_{cb1}/(L_0 + L_{2\_1})\lambda_1^2}\right)}. \quad (6)$$

5. The viscosity measuring method according to claim 4, wherein the step of obtaining the flow behavior index n includes:

a step in which a provisional flow behavior index $n_a$ is determined;

a step in which, based on the above Expressions (3) to (5) established among:

the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio $\kappa$; and a first dimensionless coordinate $\lambda_1$; or based on a graph or a table created based on the above Expressions (3) to (5), the first dimensionless coordinate $\lambda_1$ is obtained;

a step in which, based on the above Expression (2) established among the provisional flow behavior index $n_a$, the first dimensionless coordinate $\lambda_1$ and a first dimensionless flow velocity $\Phi_1$, or based on a graph or a table created based on the above Expression (2), the first dimensionless flow velocity $\Phi_1$ is obtained;

a step in which, based on the above Expressions (3) to (5) established among: the provisional flow behavior index $n_a$; the second relative movement distance $\Delta L_2$, the second peak value $F_{T2}$ and the second convergent value $F_{Te2}$, at the second relative movement velocity $v_{p2}$; the plunger ratio $\kappa$; and a second dimensionless coordinate $\lambda_2$; or based on a graph or a table created based on the above Expressions (3) to (5), the second dimensionless coordinate $\lambda_2$ is obtained;

a step in which, based on the above Expression (2) established among the provisional flow behavior index $n_a$, the second dimensionless coordinate $\lambda_2$ and a second dimensionless flow velocity $\Phi_2$, or based on a graph or a table created based on the above Expression (2), the second dimensionless flow velocity $\Phi_2$ is obtained;

a step in which a flow behavior index n is obtained based on: the first dimensionless coordinate $\lambda_1$ and the first dimensionless flow velocity $\Phi_1$ at the first relative movement velocity $v_{p1}$; the second dimensionless coordinate $\lambda_2$ and the second dimensionless flow velocity $\Phi_2$ at the second relative movement velocity $v_{p2}$; and the above Expression (6); and a step in which the method returns to the step of determining a provisional flow behavior index $n_a$, when the obtained flow behavior index n is compared to the provisional flow behavior index $n_a$ to find out that the obtained flow behavior index n is different from the provisional flow behavior index $n_a$.

6. A method of measuring an apparent viscosity of a sample of non-Newtonian fluid comprising:

(A) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;

(B) a step in which the plunger is further immersed into the sample coaxially with the cylindrical container at a first relative movement velocity $v_{p1}$ by a relative movement distance $\Delta L$, and during the further immersing operation and after the further immersing operation, a force applied to the plunger from the sample is measured with a passage of time;

(C) a step in which a first peak value $F_{T1}$ and a first convergent value $F_{Te1}$ of the force applied to the plunger from the sample are obtained, based on measured values of the force caused by the relative movement of the plunger at the first relative movement velocity $v_{p1}$;

(D) a step in which the plunger is returned coaxially with the cylindrical container to the initial depth $L_0$ and stopped thereat;

(E) a step in which the plunger is further immersed into the sample coaxially with the cylindrical container at a second relative movement velocity $v_{p2}$ by the relative movement distance $\Delta L$, and during the further immersing operation and after the further immersing operation, a force applied to the plunger from the sample is measured with a passage of time;

(F) a step in which a second peak value $F_{T2}$ and a second convergent value $F_{Te2}$ of the force applied to the plunger from the sample are obtained, based on measured values of the force caused by the relative movement of the plunger at the second relative movement velocity $v_{p2}$;

(G) a step in which, based on a predetermined relationship established among: the first peak value $F_{T1}$ and the first convergent value $F_{Te1}$ at the first relative movement velocity $v_{p1}$; the second peak value $F_{T2}$ and the second convergent value $F_{Te2}$ at the second relative movement velocity $v_{p2}$; the relative movement distance $\Delta L$; a plunger ratio $\kappa = R_i/R_0$; and a flow behavior index n of the sample; the flow behavior index n is obtained;

(H) a step in which, when the first relative movement velocity $v_{p1}$ is represented as $v_p$, the first peak value $F_{T1}$ is represented as $F_T$, and the first convergent value $F_{Te1}$ is represented as $F_{Te}$, or when the second relative movement velocity $v_{p2}$ is represented as $v_p$, the second peak value $F_{T2}$ is represented as $F_T$, and the second convergent value $F_{Te2}$ is represented as $F_{Te}$, an apparent viscosity $\mu_a$ of the sample is calculated based on the $v_p$, the $F_T$, the $F_{Te}$, the relative movement distance $\Delta L$, the plunger ratio $\kappa$, the flow behavior index n, a density $\rho$ of the sample, a gravitational acceleration g, and the following Expression (1):

[NO 3]

$$\mu_a = \frac{\sigma_w}{dy/dt} = \frac{\sigma_0 + K\left(\frac{dy}{dt}\right)^n}{dy/dt} \tag{1}$$

in which $$\sigma_w = \frac{T_w P R_0}{2}, \quad \frac{dy}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, \quad P = \frac{2\sigma_y}{T_0 R_0}, \quad T_w = \frac{\lambda^2}{\kappa} - \kappa,$$

$$\Phi = \left\{\int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx\right\}\kappa^2 - \tag{2}$$

$$\int_\kappa^{\lambda_-}(\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx, \tag{3}$$

$$s = \frac{1}{n},$$

$$\lambda_- = \frac{1}{2}\left[(T_0^2 + 4\lambda^2)^{\frac{1}{2}} - T_0\right], \tag{4}$$

$$\lambda_+ = \frac{1}{2}\left[(T_0^2 + 4\lambda^2)^{\frac{1}{2}} + T_0\right], \tag{5}$$

$$T_0 = \frac{F_y}{F_{cb}}, \quad \sigma_y = \frac{F_y}{2\pi R_i(L_0 + L_2)}, \quad F_y = F_{Te} - F_b,$$

$$F_{cb} = F_T - F_b, \quad F_b = \pi R_i^2 L_2 \rho g, \quad L_2 = \frac{\Delta L}{1 - \kappa^2}.$$

7. A method of measuring an apparent viscosity of a sample of non-Newtonian fluid comprising:

(A) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;

(B) a step in which the plunger is further immersed into the sample coaxially with the cylindrical container at a first relative movement velocity $v_{p1}$ by a first relative movement distance $\Delta L_1$, and during the further immersing operation and after the further immersing operation, a force applied to the plunger from the sample is measured with a passage of time;

(C) a step in which a first peak value $F_{T1}$ and a first convergent value $F_{Te1}$ of the force applied to the plunger from the sample are obtained, based on measured values of the force caused by the relative movement of the plunger at the first relative movement velocity $v_{p1}$;

(D) a step in which the plunger is returned coaxially with the cylindrical container to the initial depth $L_0$ and stopped thereat;

(E) a step in which the plunger is further immersed into the sample coaxially with the cylindrical container at a second relative movement velocity $v_{p2}$ by a second relative movement distance $\Delta L_2$, and during the further immersing operation and after the further immersing operation, a force applied to the plunger from the sample is measured with a passage of time;

(F) a step in which a second peak value $F_{T2}$ and a second convergent value $F_{Te2}$ of the force applied to the plunger from the sample are obtained, based on measured values of the force caused by the relative movement of the plunger at the second relative movement velocity $v_{p2}$;

(G) a step in which, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n is obtained;

(H) a step in which the plunger is returned coaxially with the cylindrical container to the initial depth $L_0$ and stopped thereat;

(I) a step in which the plunger is further immersed into the sample coaxially with the cylindrical container at a third relative movement velocity $v_{p3}$ by a third relative movement distance $\Delta L_3$, and during the further immersing operation and after the further immersing operation, a force applied to the plunger from the sample is measured with a passage of time;

(J) a step in which a third peak value $F_{T3}$ and a third convergent value $F_{Te3}$ of the force applied to the plunger from the sample are obtained, based on measured values of the force caused by the relative movement of the plunger at the third relative movement velocity $v_{p3}$;

(K) a step in which, when the third relative movement velocity $v_{p3}$ is represented as $v_p$, the third relative movement distance $\Delta L_3$ is represented as $\Delta L$, the third peak value $F_{T3}$ is represented as $F_T$ and the third convergent value $F_{Te3}$ is represented as $F_{Te}$, an apparent viscosity $\mu_a$ of the sample is calculated based on the $v_p$, the $\Delta L$, the $F_T$ and the $F_{Te}$, the plunger ratio $\kappa$, the flow behavior index n, a density $\rho$ of the sample, a gravitational acceleration g, and the following Expression (1):

[NO 4]

$$\mu_a = \frac{\sigma_w}{dy/dt} = \frac{\sigma_0 + K\left(\frac{dy}{dt}\right)^n}{dy/dt} \quad (1)$$

in which $$\sigma_w = \frac{T_w P R_0}{2}, \quad \frac{dy}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, \quad P = \frac{2\sigma_y}{T_0 R_0}, \quad T_w = \frac{\lambda^2}{\kappa} - \kappa,$$

$$\Phi = \left\{\int_\kappa^{\lambda_-}(\lambda^2 - x^2 - T_0 x)^s x^{-s}dx - \int_{\lambda_+}^1 (x^2 - \lambda^2 - T_0 x)^s x^{-s}dx\right\}\kappa^2 - \quad (2)$$

$$\int_\kappa^{\lambda_-}(\lambda^2 - x^2 - T_0 x)^s x^{2-s}dx + \int_{\lambda_+}^1 (x^2 - \lambda^2 - T_0 x)^s x^{2-s}dx$$

-continued $$0 = \int_\kappa^{\lambda_-}(\lambda^2 - x^2 - T_0 x)^s x^{-s}dx - \int_{\lambda_+}^1 (x^2 - \lambda^2 - T_0 x)^s x^{-s}dx, \quad (3)$$

$$s = \frac{1}{n},$$

$$\lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \quad \sigma_y = \frac{F_y}{2\pi R_i(L_0 + L_2)}, \quad F_y = F_{Te} - F_b,$$

$$F_{cb} = F_T - F_b, \quad F_b = \pi R_i^2 L_2 \rho g, \quad L_2 = \frac{\Delta L}{1 - \kappa^2}.$$

8. A viscosity measuring apparatus comprising:
a cylindrical container having a predetermined inner radius $R_0$, in which a sample is contained;
a plunger having an outer radius $R_i$ that is smaller than the inner radius $R_0$ of the cylindrical container, the plunger being arranged inside the cylindrical container coaxially therewith so as to be relatively movable;
a driving unit configured to relatively move the plunger coaxially with the cylindrical container;
a measuring unit disposed on the plunger and configured to measure a force applied to the plunger from the sample; and
a control unit configured to control the driving unit;
wherein:
the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;
the measuring unit is configured to measure a force applied to the plunger from the sample with a passage of time, during the further immersing operation of the plunger at the first relative movement velocity $v_{p1}$ and after the further immersing operation thereof;
the control unit is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;
the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;
the measuring unit is configured to measure a force applied to the plunger from the sample with a passage of time, during the further immersing operation of the plunger at the second relative movement velocity $v_{p2}$ and after the further immersing operation thereof;
the control unit is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control unit is further configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio is $\kappa = R_i/R_0$; and a flow behavior index n of the sample; the flow behavior index n; and the control unit is further configured to calculate, when the first relative movement velocity $v_{p1}$ is represented as $v_p$, the first relative movement distance $\Delta L_1$ is represented as $\Delta L$, the first peak value $F_{T1}$ is represented as $F_T$, and the first convergent value $F_{Te1}$ is represented as $F_{Te}$, or when the second relative movement velocity $v_{p2}$ is represented as $v_p$, the second relative movement distance $\Delta L_2$ is represented as $\Delta L$, the second peak value $F_{T2}$ is represented as $F_T$, and the second convergent value $F_{Te2}$ is represented as $F_{Te}$, an apparent viscosity $\mu_a$ of the sample based on the $v_p$, the $\Delta L$, the $F_T$, the $F_{Te}$, the plunger ratio $\kappa$, the flow behavior index n, a density $\rho$ of the sample, a gravitational acceleration g, and the following Expression (1):

[NO 5]

$$\mu_a = \frac{\sigma_w}{dy/dt} = \frac{\sigma_0 + K\left(\frac{dy}{dt}\right)^n}{dy/dt} \qquad (1)$$

in which $$\sigma_w = \frac{T_w P R_0}{2}, \quad \frac{dy}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, \quad P = \frac{2\sigma_y}{T_0 R_0}, \quad T_w = \frac{\lambda^2}{\kappa} - \kappa,$$

$$\Phi = \left\{\int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx\right\}\kappa^2 - \qquad (2)$$
$$\int_\kappa^{\lambda_-}(\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-}(\lambda^2 - x^2 - T_0 x)^s x^{-s} dx - \int_{\lambda_+}^1 (x^2 - \lambda^2 - T_0 x)^s x^{-s} dx, \qquad (3)$$

$$s = \frac{1}{n},$$

$$\lambda_- = \frac{1}{2}\left[(T_0^2 + 4\lambda^2)^{\frac{1}{2}} - T_0\right], \qquad (4)$$

$$\lambda_+ = \frac{1}{2}\left[(T_0^2 + 4\lambda^2)^{\frac{1}{2}} + T_0\right], \qquad (5)$$

$$T_0 = \frac{F_y}{F_{cb}}, \quad \sigma_y = \frac{F_y}{2\pi R_i(L_0 + L_2)}, \quad F_y = F_{Te} - F_b,$$

$$F_{cb} = F_T - F_b, \quad F_b = \pi R_i^2 L_2 \rho g, \quad L_2 = \frac{\Delta L}{1-\kappa^2}.$$

9. The viscosity measuring apparatus according to claim 8, wherein
the first relative movement distance $\Delta L_1$ and the second relative movement distance $\Delta L_2$ are smaller than the initial depth $L_0$.

10. The viscosity measuring apparatus according to claim 8, wherein before the control unit obtains the flow behavior index n, the control unit is configured to judge whether the convergent value $F_{Te}$ of the force applied to the plunger from the sample at the first relative movement velocity $v_{p1}$ or the second relative movement velocity $v_{p2}$ is larger or not than a buoyancy force $F_b$ applied to the plunger from the sample, and when the control unit judges that the convergent value $F_{Te}$ is larger than the buoyancy force $F_b$, the control unit is configured to perform the process for obtaining the flow behavior index n.

11. The viscosity measuring apparatus according to claim 8, wherein
the relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; the plunger ratio $\kappa$; and the flow behavior index n of the sample includes the above Expressions (2) to (5) and the following Expression (6):

[NO 6]

$$s = \frac{1}{n} = \frac{\ln\left(\frac{v_{p2}/\Phi_2}{v_{p1}/\Phi_1}\right)}{\ln\left(\frac{F_{cb2}/(L_0 + L_{2\_2})\lambda_2^2}{F_{cb1}/(L_0 + L_{2\_1})\lambda_1^2}\right)}. \qquad (6)$$

12. The viscosity measuring apparatus according to claim 11, wherein
when the control unit obtains the flow behavior index n, the control unit is configured:
to determine a provisional flow behavior index $n_a$;
to obtain, based on the above Expressions (3) to (5) established among: the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio $\kappa$; and a first dimensionless coordinate $\lambda_1$; or based on a graph or a table created based on the above Expressions (3) to (5), the first dimensionless coordinate $\lambda_1$;
to obtain, based on the above Expression (2) established among the provisional flow behavior index $n_a$, the first dimensionless coordinate $\lambda_1$ and a first dimensionless flow velocity $\Phi_1$, or based on a graph or a table created based on the above Expression (2), the first dimensionless flow velocity $\Phi_1$;
to obtain, based on the above Expressions (3) to (5) established among: the provisional flow behavior index $n_a$; the second relative movement distance $\Delta L_2$, the second peak value $F_{T2}$ and the second convergent value $F_{Te2}$, at the second relative movement velocity $v_{p2}$; the plunger ratio $\kappa$; and a second dimensionless coordinate $\lambda_2$; or based on a graph or a table created based on the above Expressions (3) to (5), the second dimensionless coordinate $\lambda_2$;
to obtain, based on the above Expression (2) established among the provisional flow behavior index $n_a$, the second dimensionless coordinate $\lambda_2$ and a second dimensionless flow velocity $\Phi_2$, or based on a graph or a table created based on the above Expression (2), the second dimensionless flow velocity $\Phi_2$;

to obtain a flow behavior index n based on: the first dimensionless coordinate) $\lambda_i$ and the first dimensionless flow velocity $\Phi_1$ at the first relative movement velocity $v_{p1}$; the second dimensionless coordinate $\lambda_2$ and the second dimensionless flow velocity $\Phi_2$ at the second relative movement velocity $v_{p2}$; and the above Expression (6); and to return to the step of determining a provisional flow behavior index $n_a$, when the control unit compares the obtained flow behavior index n to the provisional flow behavior index $n_a$ to find out that the obtained flow behavior index n is different from the provisional flow behavior index $n_a$.

13. A viscosity measuring apparatus comprising:
a cylindrical container having a predetermined inner radius $R_0$, in which a sample is contained;
a plunger having an outer radius $R_i$ that is smaller than the inner radius $R_0$ of the cylindrical container, the plunger being arranged inside the cylindrical container coaxially therewith so as to be relatively movable;
a driving unit configured to relatively move the plunger coaxially with the cylindrical container;
a measuring unit disposed on the plunger and configured to measure a force applied to the plunger from the sample; and
a control unit configured to control the driving unit; wherein:
the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a relative movement distance $\Delta L$;
the measuring unit is configured to measure a force applied to the plunger from the sample with a passage of time, during the further immersing operation of the plunger at the first relative movement velocity $v_{p1}$ and after the further immersing operation thereof;
the control unit is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;
the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by the relative movement distance $\Delta L$;
the measuring unit is configured to measure a force applied to the plunger from the sample with a passage of time, during the further immersing operation of the plunger at the second relative movement velocity $v_{p2}$ and after the further immersing operation thereof;
the control unit is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;
the control unit is further configured to obtain, based on a predetermined relationship established among: the first peak value $F_{T1}$ and the first convergent value $F_{Te1}$, at the first relative movement velocity $v_{p1}$; the second peak value $F_{T2}$ and the second convergent value $F_{Te2}$, at the second relative movement velocity $v_{p2}$; the relative movement distance $\Delta L$; a plunger ratio $\kappa = R_i/R_0$; and a flow behavior index n of the sample; the flow behavior index n; and the control unit is further configured, when the first relative movement velocity $v_{p1}$ is represented as $v_p$, the first peak value $F_{T1}$ is represented as $F_T$, and the first convergent value $F_{Te1}$ is represented as $F_{Te}$, or when the second relative movement velocity $v_{p2}$ is represented as $v_p$, the second peak value $F_{T2}$ is represented as $F_T$, and the second convergent value $F_{Te2}$ is represented as $F_{Te}$, to calculate an apparent viscosity $\mu_a$ of the sample based on the $v_p$, the $F_T$, the $F_{Te}$, the relative movement distance $\Delta L$, the plunger ratio $\kappa$, the flow behavior index n, a density $\rho$ of the sample, a gravitational acceleration g, and the following Expression (1):

[NO 7]

$$\mu_a = \frac{\sigma_w}{dy/dt} = \frac{\sigma_0 + K\left(\frac{dy}{dt}\right)^n}{dy/dt} \tag{1}$$

in which $$\sigma_w = \frac{T_w PR_0}{2}, \quad \frac{dy}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, \quad P = \frac{2\sigma_y}{T_0 R_0}, \quad T_w = \frac{\lambda^2}{\kappa} - \kappa,$$

$$\Phi = \left\{\int_\kappa^{\lambda_-}(\lambda^2 - x^2 - T_0 x)^s x^{-s}\, dx - \int_{\lambda_+}^1 (x^2 - \lambda^2 - T_0 x)^s x^{-s}\, dx\right\}\kappa^2 - \tag{2}$$

$$\int_\kappa^{\lambda_-}(\lambda^2 - x^2 - T_0 x)^s x^{2-s}\, dx + \int_{\lambda_+}^1 (x^2 - \lambda^2 - T_0 x)^s x^{2-s}\, dx$$

$$0 = \int_\kappa^{\lambda_-}(\lambda^2 - x^2 - T_0 x)^s x^{-s}\, dx - \int_{\lambda_+}^1 (x^2 - \lambda^2 - T_0 x)^s x^{-s}\, dx, \tag{3}$$

$$s = \frac{1}{n},$$

$$\lambda_- = \frac{1}{2}\left[(T_0^2 + 4\lambda^2)^{\frac{1}{2}} - T_0\right], \tag{4}$$

$$\lambda_+ = \frac{1}{2}\left[(T_0^2 + 4\lambda^2)^{\frac{1}{2}} + T_0\right], \tag{5}$$

$$T_0 = \frac{F_y}{F_{cb}}, \quad \sigma_y = \frac{F_y}{2\pi R_i(L_0 + L_2)}, \quad F_y = F_{Te} - F_b,$$

$$F_{cb} = F_T - F_b, \quad F_b = \pi R_i^2 L_2 \rho g, \quad L_2 = \frac{\Delta L}{1 - \kappa^2}.$$

14. A viscosity measuring apparatus comprising:
a cylindrical container having a predetermined inner radius $R_0$, in which a sample is contained;
a plunger having an outer radius $R_i$ that is smaller than the inner radius $R_0$ of the cylindrical container, the plunger being arranged inside the cylindrical container coaxially therewith so as to be relatively movable;
a driving unit configured to relatively move the plunger coaxially with the cylindrical container;
a measuring unit disposed on the plunger and configured to measure a force applied to the plunger from the sample; and
a control unit configured to control the driving unit;

wherein:
the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control unit is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control unit is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control unit is further configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n;

the control unit is further configured to control the driving unit such that the plunger is returned coaxially with the cylindrical container to the initial depth $L_0$ and stopped thereat, and that the plunger is then further immersed into the sample coaxially with the cylindrical container at a third relative movement velocity $v_{p3}$ by a third relative movement distance $\Delta L_3$;

the measuring unit is configured to measure a force applied to the plunger from the sample with a passage of time, during the further immersing operation of the plunger at the third relative movement velocity $v_{p3}$ and after the further immersing operation thereof;

the control unit is configured to obtain a third peak value $F_{T3}$ and a third convergent value $F_{Te3}$ of the force applied to the plunger from the sample, based on measured values of the force caused by the relative movement of the plunger at the third relative movement velocity $v_{p3}$; and the control unit is further configured to calculate, when the third relative movement velocity $v_{p3}$ is represented as $v_p$, the third relative movement distance $\Delta L_3$ is represented as $\Delta L$, the third peak value $F_{T3}$ is represented as $F_T$ and the third convergent value $F_{Te3}$ is represented as $F_{Te}$, an apparent viscosity $\mu_a$ of the sample based on the $v_p$, the $\Delta L$, the $F_T$ and the $F_{Te}$, the plunger ratio $\kappa$, the flow behavior index n, a density $\rho$ of the sample, a gravitational acceleration g, and the following Expression (1):

[NO 8]

$$\mu_a = \frac{\sigma_w}{dy/dt} = \frac{\sigma_0 + K\left(\frac{dy}{dt}\right)^n}{dy/dt} \quad (1)$$

in which $$\sigma_w = \frac{T_w P R_0}{2}, \quad \frac{dy}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, \quad P = \frac{2\sigma_y}{T_0 R_0}, \quad T_w = \frac{\lambda^2}{\kappa} - \kappa,$$

$$\Phi = \left\{\int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx\right\} \kappa^2 - \quad (2)$$
$$\int_\kappa^{\lambda_-} (\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx, \quad (3)$$

$$s = \frac{1}{n},$$

$$\lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \quad \sigma_y = \frac{F_y}{2\pi R_i (L_0 + L_2)}, \quad F_y = F_{Te} - F_b,$$

$$F_{cb} = F_T - F_b, \quad F_b = \pi R_i^2 L_2 \rho g, \quad L_2 = \frac{\Delta L}{1 - \kappa^2}.$$

15. A control apparatus for controlling a viscosity measuring apparatus including:
a cylindrical container having a predetermined inner radius $R_0$, in which a sample is contained;
a plunger having an outer radius $R_i$ that is smaller than the inner radius $R_0$ of the cylindrical container, the plunger being arranged inside the cylindrical container coaxially therewith so as to be relatively movable;
a driving unit configured to relatively move the plunger coaxially with the cylindrical container; and
a measuring unit disposed on the plunger and configured to measure a force applied to the plunger from the sample;

wherein:
the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control apparatus is further configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n;

the control apparatus is further configured to calculate, when the first relative movement velocity $v_{p1}$ is represented as $v_p$, the first relative movement distance $\Delta L_1$ is represented as $\Delta L$, the first peak value $F_{T1}$ is represented as $F_T$, and the first convergent value $F_{Te1}$ is represented as $F_{Te}$, or when the second relative movement velocity $v_{p2}$ is represented as $v_p$, the second relative movement distance $\Delta L_2$ is represented as $\Delta L$, the second peak value $F_{T2}$ is represented as $F_T$, and the second convergent value $F_{Te2}$ is represented as $F_{Te}$, an apparent viscosity $\mu_a$ of the sample based on the $v_p$, the $\Delta L$, the $F_T$, the $F_{Te}$, the plunger ratio $\kappa$, the flow behavior index n, a density $\rho$ of the sample, a gravitational acceleration g, and the following Expression (1):

[NO 9]

$$\mu_a = \frac{\sigma_w}{dy/dt} = \frac{\sigma_0 + K\left(\frac{dy}{dt}\right)^n}{dy/dt} \tag{1}$$

in which $$\sigma_w = \frac{T_w P R_0}{2}, \frac{dy}{dt} = \left(\frac{\lambda^2}{\kappa} - \kappa - T_0\right)^s \left(\frac{P R_0}{2K}\right)^s,$$

$$K = \frac{P R_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

-continued $$\Phi = \left\{\int_\kappa^{\lambda_-}(\lambda^2 - x^2 - T_0 x)^s x^{-s} dx - \int_{\lambda_+}^{1}(x^2 - \lambda^2 - T_0 x)^s x^{-s} dx\right\} \kappa^2 - \tag{2}$$

$$\int_\kappa^{\lambda_-}(\lambda^2 - x^2 - T_0 x)^s x^{2-s} dx + \int_{\lambda_+}^{1}(x^2 - \lambda^2 - T_0 x)^s x^{2-s} dx$$

$$0 = \int_\kappa^{\lambda_-}(\lambda^2 - x^2 - T_0 x)^s x^{-s} dx - \int_{\lambda_+}^{1}(x^2 - \lambda^2 - T_0 x)^s x^{-s} dx, \tag{3}$$

$$s = \frac{1}{n},$$

$$\lambda_- = \frac{1}{2}\left[(T_0^2 + 4\lambda^2)^{\frac{1}{2}} - T_0\right], \tag{4}$$

$$\lambda_+ = \frac{1}{2}\left[(T_0^2 + 4\lambda^2)^{\frac{1}{2}} + T_0\right], \tag{5}$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

16. The control apparatus according to claim 15, wherein the first relative movement distance $\Delta L_1$ and the second relative movement distance $\Delta L_2$ are smaller than the initial depth $L_0$.

17. The control apparatus according to claim 15, configured to judge, before the control apparatus obtains the flow behavior index n, whether the convergent value $F_{Te}$ of the force applied to the plunger from the sample at the first relative movement velocity $v_{p1}$ or the second relative movement velocity $v_{p2}$ is larger or not than a buoyancy force $F_b$ applied to the plunger from the sample, and configured to perform the process for obtaining the flow behavior index n, when the control apparatus judges that the convergent value $F_{Te}$ is larger than the buoyancy force $F_b$.

18. The control apparatus according to claim 15, wherein the relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; the plunger ratio $\kappa$; and the flow behavior index n of the sample includes the above Expressions (2) to (5) and the following Expression (6):

[NO 10]

$$s = \frac{1}{n} = \frac{\ln\left(\frac{v_{p2}/\Phi_2}{v_{p1}/\Phi_1}\right)}{\ln\left(\frac{F_{cb2}/(L_0 + L_{2\_2})\lambda_2^2}{F_{cb1}/(L_0 + L_{2\_1})\lambda_1^2}\right)}. \tag{6}$$

19. The control apparatus according to claim 18,
when the control apparatus obtains the flow behavior index n, the control apparatus is configured:
to determine a provisional flow behavior index $n_a$;
to obtain, based on the above Expressions (3) to (5) established among: the provisional flow behavior index $n_a$; the first relative movement distance $\Delta L_1$, the first peak value $F_{T1}$ and the first convergent value $F_{Te1}$, at the first relative movement velocity $v_{p1}$; the plunger ratio $\kappa$; and a first dimensionless coordinate $\lambda_1$; or based on a graph or a table created based on the above Expressions (3) to (5), the first dimensionless coordinate $\lambda_1$;

to obtain, based on the above Expression (2) established among the provisional flow behavior index $n_a$, the first dimensionless coordinate $\lambda_1$ and a first dimensionless flow velocity $\Phi_1$, or based on a graph or a table created based on the above Expression (2), the first dimensionless flow velocity $\Phi_1$;

to obtain, based on the above Expressions (3) to (5) established among: the provisional flow behavior index $n_a$; the second relative movement distance $\Delta L_2$, the second peak value $F_{T2}$ and the second convergent value $F_{Te2}$, at the second relative movement velocity $v_{p2}$; the plunger ratio $\kappa$; and a second dimensionless coordinate $\lambda_2$;

or based on a graph or a table created based on the above Expressions (3) to (5), the second dimensionless coordinate $\lambda_2$;

to obtain, based on the above Expression (2) established among the provisional flow behavior index $n_a$, the second dimensionless coordinate $\lambda_2$ and a second dimensionless flow velocity $\Phi_2$, or based on a graph or a table created based on the above Expression (2), the second dimensionless flow velocity $\Phi_2$;

to obtain a flow behavior index n based on: the first dimensionless coordinate $\lambda_1$ and the first dimensionless flow velocity $\Phi_1$ at the first relative movement velocity $v_{p1}$; the second dimensionless coordinate $\lambda_2$ and the second dimensionless flow velocity $\Phi_2$ at the second relative movement velocity $v_{p2}$; and the above Expression (6); and to return to the step of determining a provisional flow behavior index $n_a$, when the control apparatus compares the obtained flow behavior index n to the provisional flow behavior index $n_a$ to find out that the obtained flow behavior index n is different from the provisional flow behavior index $n_a$.

20. A control apparatus for controlling a viscosity measuring apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container; and a measuring unit disposed on the plunger and configured to measure a force applied to the plunger from the sample;

wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a relative movement distance $\Delta L$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by the relative movement distance $\Delta L$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;

the control apparatus is further configured to obtain, based on a predetermined relationship established among: the first peak value $F_{T1}$ and the first convergent value $F_{Te1}$, at the first relative movement velocity $v_{p1}$; the second peak value $F_{T2}$ and the second convergent value $F_{Te2}$, at the second relative movement velocity $v_{p2}$; the relative movement distance $\Delta L$; a plunger ratio $\kappa = R_i/R_0$; and a flow behavior index n of the sample; the flow behavior index n; and the control apparatus is further configured to calculate, when the first relative movement velocity $v_{p1}$ is represented as $v_p$, the first peak value $F_{T1}$ is represented as $F_T$, and the first convergent value $F_{Te1}$ is represented as $F_{Te}$, or when the second relative movement velocity $v_{p2}$ is represented as $v_p$, the second peak value $F_{T2}$ is represented as $F_T$, and the second convergent value $F_{Te2}$ is represented as $F_{Te}$, an apparent viscosity $\mu_a$ of the sample based on the $v_p$, the $F_T$, the $F_{Te}$, the relative movement distance $\Delta L$, the plunger ratio $\kappa$, the flow behavior index n, a density $\rho$ of the sample, a gravitational acceleration g, and the following Expression (1):

[NO 11]

$$\mu_a = \frac{\sigma_w}{dy/dt} = \frac{\sigma_0 + K\left(\frac{dy}{dt}\right)^n}{dy/dt} \tag{1}$$

in which $$\sigma_w = \frac{T_w P R_0}{2}, \quad \frac{dy}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, \quad P = \frac{2\sigma_y}{T_0 R_0}, \quad T_w = \frac{\lambda^2}{\kappa} - \kappa,$$

$$\Phi = \left\{\int_\kappa^{\lambda_-} (\lambda^2 - x^2 - T_0 x)^s x^{-s} dx - \int_{\lambda_+}^{1} (x^2 - \lambda^2 - T_0 x)^s x^{-s} dx\right\}\kappa^2 - \tag{2}$$

$$\int_\kappa^{\lambda_-} (\lambda^2 - x^2 - T_0 x)^s x^{2-s} dx + \int_{\lambda_+}^{1} (x^2 - \lambda^2 - T_0 x)^s x^{2-s} dx$$

$$0 = \int_\kappa^{\lambda_-} (\lambda^2 - x^2 - T_0 x)^s x^{-s} dx - \int_{\lambda_+}^{1} (x^2 - \lambda^2 - T_0 x)^s x^{-s} dx, \tag{3}$$

$$s = \frac{1}{n},$$

-continued $$\lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

21. A control apparatus for controlling a viscosity measuring apparatus including:
- a cylindrical container having a predetermined inner radius $R_0$, in which a sample is contained;
- a plunger having an outer radius $R_i$ that is smaller than the inner radius $R_0$ of the cylindrical container, the plunger being arranged inside the cylindrical container coaxially therewith so as to be relatively movable;
- a driving unit configured to relatively move the plunger coaxially with the cylindrical container; and
- a measuring unit disposed on the plunger and configured to measure a force applied to the plunger from the sample;

wherein:
- the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;
- the measuring unit is configured to measure a force applied to the plunger from the sample with a passage of time, during the further immersing operation of the plunger at the first relative movement velocity $v_{p1}$ and after the further immersing operation thereof;
- the control apparatus is configured to obtain a first peak value $F_{T1}$ and a first convergent value $F_{Te1}$ of the force applied to the plunger from the sample, based on measured values of the force caused by the relative movement of the plunger at the first relative movement velocity $v_{p1}$;
- the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;
- the measuring unit is configured to measure a force applied to the plunger from the sample with a passage of time, during the further immersing operation of the plunger at the second relative movement velocity $v_{p2}$ and after the further immersing operation thereof;
- the control apparatus is configured to obtain a second peak value $F_{T2}$ and a second convergent value $F_{Te2}$ of the force applied to the plunger from the sample, based on measured values of the force caused by the relative movement of the plunger at the second relative movement velocity $v_{p2}$;
- the control apparatus is further configured to obtain, based on a predetermined relationship established among: the first relative movement distance $\Delta L_1$, the first peak value $F_{T1}$ and the first convergent value $F_{Te1}$, at the first relative movement velocity $v_{p1}$; the second relative movement distance $\Delta L_2$, the second peak value $F_{T2}$ and the second convergent value $F_{Te2}$, at the second relative movement velocity $v_{p2}$; a plunger ratio $\kappa = R_i/R_0$; and a flow behavior index n of the sample; the flow behavior index n;
- the control apparatus is further configured to control the driving unit such that the plunger is returned coaxially with the cylindrical container to the initial depth $L_0$ and stopped thereat, and that the plunger is then further immersed into the sample coaxially with the cylindrical container at a third relative movement velocity $v_{p3}$ by a third relative movement distance $\Delta L_3$;
- the measuring unit is configured to measure a force applied to the plunger from the sample with a passage of time, during the further immersing operation of the plunger at the third relative movement velocity $v_{p3}$ and after the further immersing operation thereof;
- the control apparatus is configured to obtain a third peak value $F_{T3}$ and a third convergent value $F_{Te3}$ of the force applied to the plunger from the sample, based on measured values of the force caused by the relative movement of the plunger at the third relative movement velocity $v_{p3}$; and
- the control apparatus is further configured to calculate, when the third relative movement velocity $v_{p3}$ is represented as $v_p$, the third relative movement distance $\Delta L_3$ is represented as $\Delta L$, the third peak value $F_{T3}$ is represented as $F_T$ and the third convergent value $F_{Te3}$ is represented as $F_{Te}$, an apparent viscosity $\mu_a$ of the sample based on the $v_p$, the $\Delta L$, the $F_T$ and the $F_{Te}$, the plunger ratio $\kappa$, the flow behavior index n, a density $\rho$ of the sample, a gravitational acceleration g, and the following Expression (1):

[NO 12]

$$\mu_a = \frac{\sigma_w}{dy/dt} = \frac{\sigma_0 + K\left(\frac{dy}{dt}\right)^n}{dy/dt} \quad (1)$$

in which $$\sigma_w = \frac{T_w PR_0}{2}, \frac{dy}{dt} = \left(\frac{\lambda^2}{\kappa} - \kappa - T_0\right)^s \left(\frac{PR_0}{2K}\right)^s,$$

$$K = \frac{PR_0}{2}\left(\frac{\Phi R_0}{v_p \kappa^2}\right)^n, P = \frac{2\sigma_y}{T_0 R_0}, T_w = \frac{\lambda^2}{\kappa} - \kappa,$$

$$\Phi = \left\{\int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx\right\} \kappa^2 - \quad (2)$$

$$\int_\kappa^{\lambda_-} (\lambda^2 - x^2 - T_0 x)^s x^{2-s} dx + \int_{\lambda_+}^1 (x^2 - \lambda^2 - T_0 x)^s x^{2-s} dx$$

$$0 = \int_\kappa^{\lambda_-} (\lambda^2 - x^2 - T_0 x)^s x^{-s} dx - \int_{\lambda_+}^1 (x^2 - \lambda^2 - T_0 x)^s x^{-s} dx, \quad (3)$$

$$s = \frac{1}{n},$$

$$\lambda_- = \frac{1}{2}\left[(T_0^2 + 4\lambda^2)^{\frac{1}{2}} - T_0\right], \quad (4)$$

$$\lambda_+ = \frac{1}{2}\left[(T_0^2 + 4\lambda^2)^{\frac{1}{2}} + T_0\right], \quad (5)$$

$$T_0 = \frac{F_y}{F_{cb}}, \sigma_y = \frac{F_y}{2\pi R_i(L_0 + L_2)}, F_y = F_{Te} - F_b,$$

$$F_{cb} = F_T - F_b, F_b = \pi R_i^2 L_2 \rho g, L_2 = \frac{\Delta L}{1 - \kappa^2}.$$

* * * * *